US009782389B2

(12) United States Patent
Underhill et al.

(10) Patent No.: US 9,782,389 B2
(45) Date of Patent: *Oct. 10, 2017

(54) FUNGAL MYCOBIOME AS PROBIOTICS, DIAGNOSTICS AND THERAPEUTICS

(71) Applicant: Cedars-Sinai Medical Center, Los Angeles, CA (US)

(72) Inventors: David M. Underhill, Tarzana, CA (US); Iliyan D. Iliev, West Hollywood, CA (US)

(73) Assignee: CEDARS-SINAI MEDICAL CENTER, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/213,148

(22) Filed: Jul. 18, 2016

(65) Prior Publication Data
US 2016/0317501 A1 Nov. 3, 2016

Related U.S. Application Data

(63) Continuation of application No. 14/396,468, filed as application No. PCT/US2013/038466 on Apr. 26, 2013, now Pat. No. 9,421,233.

(60) Provisional application No. 61/639,306, filed on Apr. 27, 2012.

(51) Int. Cl.
C12Q 1/68 (2006.01)
A61K 31/4196 (2006.01)
A61K 36/06 (2006.01)

(52) U.S. Cl.
CPC .......... *A61K 31/4196* (2013.01); *A61K 36/06* (2013.01); *C12Q 1/6883* (2013.01); *C12Q 1/6895* (2013.01); *C12Q 2600/118* (2013.01); *C12Q 2600/158* (2013.01)

(58) Field of Classification Search
CPC ................................................ A61K 31/4196
See application file for complete search history.

(56) References Cited

U.S. PATENT DOCUMENTS

| 8,048,404 | B1 | 11/2011 | Sung et al. | |
| 9,421,233 | B2* | 8/2016 | Underhill | A61K 36/06 |
| 2004/0028689 | A1 | 2/2004 | Borody | |
| 2009/0274662 | A1 | 11/2009 | Magowan et al. | |
| 2011/0160133 | A1 | 6/2011 | Dong et al. | |
| 2015/0110834 | A1 | 4/2015 | Underhill et al. | |

FOREIGN PATENT DOCUMENTS

| WO | 2008013374 | 1/2008 |
| WO | 2013163582 | 10/2013 |

OTHER PUBLICATIONS

Zwolinska-Wcislo et al (Journal of Physiology and Pharmacology vol. 6, No. 1, pp. 107-118, 2009).*
DeVries et al (PLoS ONE vol. 4, Issue 11, pp. 1-6, 2009).*
Foligne et al., Probiotic Yeasts: Anti-Inflammatory Potential of Various Non-Pathogenic Strains in Experimental Colitis in Mice, World J Gastroenterol, 2010, vol. 16(17), pp. 2134-2145.
Lestini et al., Trichosporon Pullul NS as a Complication of Chronic Granulomatous Disease in a Patient Undergoing Immunosuppressive Therapy for Inflammatory Bowel Disease, The Pediatric Infectious Disease Journal, 2006, vol. 25 (1), pp. 87-89.
Jawhara et al., Murine Model of Dextran Sulfate Sodium-induced Colitis Reveals Candida Glabrata Virulence and Contribution of B-Mannosyltransferases, Journal of Biological Chemistry, 2012, vol. 287(14), pp. 11313-11324.
Sebastiani et al., Spondylodiscitis Due to Candida Tropicalis as a Cause of Inflammatory Back Pain, Clin Rheumatol, 2001, vol. 20, pp. 435-437.
Tsai et al., Susceptibilities to Amphotericin B Fluconazole and Voriconazole of Trichosporon Clinical Isolates, Mycopathologia, 2012, vol. 174, pp. 121-130.
Heinsbroek et al., Genetic Deletion of dectin-1 Does Not Affect the Course of Murine Experimental Colitis, BMC Gastroenterology 2012, vol. 12(33), pp. 1-10.
Ott et al., Fungi and Inflammatory Bowel Diseases: Alterations of Composition and Diversity, Scandinavian Journal of Gastroenterology, 2008, vol. 43(7), pp. 831-841.
PCT/US2013/038466 International Search Report and Written Opinion dated Sep. 6, 2013, 9 pages.
PCT/US2013/038466 International Preliminary Report on Patentability dated Sep. 6, 2013, 7 pages.

* cited by examiner

*Primary Examiner* — Albert Navarro
(74) *Attorney, Agent, or Firm* — Linda B. Huber; Nixon Peabody LLP

(57) ABSTRACT

The present invention relates to methods of using fungal mycobiome as a means of treating and/or diagnosing diseases in a subject. In one embodiment, the present invention provides a method of diagnosing inflammatory bowel disease based on the composition of fungal strains present in the gut of a subject, and treating the subject by administering a probiotic biotherapy. In another embodiment, the present invention provides a method of diagnosing a severe form of ulcerative colitis by detecting the presence of a deficiency in dectin-1 expression in *s. fibuligera* in the gut of a subject.

7 Claims, 24 Drawing Sheets

Figure 25

| CLEC7A haplotype | MRUC Freq | Non MRUC Freq | Odds Ratio | 95% CI | p fisher |
|---|---|---|---|---|---|
| Presence of haplotype | 146/315 0.463 | 167/491 0.34 | 1.67 | 1.24-2.26 | 0.0005 |
| Homozygote for AG/AG | 29/315 0.092 | 22/491 0.045 | 2.16 | 1.17-4.03 | 0.0011 |

Figure 26

| CLEC7A haplotype | MRUC Freq | Healthy Controls Freq | Odds Ratio | 95% CI | p fisher |
|---|---|---|---|---|---|
| Presence of haplotype | 146/315 0.463 | 1138/3208 0.355 | 1.57 | 1.25-2.00 | 0.000147 |
| Homozygote for AG/AG | 29/315 0.092 | 116/3208 0.036 | 2.7 | 1.70-4.17 | 2.1 e-5 |

| CLEC7A haplotype | Non MRUC Freq | Healthy Controls Freq | Odds Ratio | 95% CI | p fisher |
|---|---|---|---|---|---|
| Presence of haplotype | 167/491 0.34 | 1138/3208 0.355 | 0.94 | 0.76-1.15 | ns |
| Homozygote for AG/AG | 22/491 0.045 | 116/3208 0.036 | 1.25 | 0.75-2.30 | ns |

FUNGAL MYCOBIOME AS PROBIOTICS, DIAGNOSTICS AND THERAPEUTICS

CROSS-REFERENCE TO RELATED APPLICATIONS

This application claims the benefit of priority under 35 U.S.C. §120 as a continuation of U.S. patent application Ser. No. 14/396,468 filed Oct. 23, 2014, now U.S. Pat. No. 9,421,233 issued Aug. 23, 2016, which is the National Phase of International Application No. PCT/US2013/038466 filed Apr. 26, 2013, now expired, which designated the U.S. and that International Application was published under PCT Article 21(2) in English. Both applications also include a claim of priority under 35 U.S.C. §119(e) to U.S. provisional patent application No. 61/639,306 filed Apr. 27, 2012, the entirety of which is hereby incorporated by reference.

GOVERNMENT RIGHTS

This invention was made with Government support under Grant No. AI071116 awarded by the National Institutes of Health. The Government has certain rights in the invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Interactions between the commensal microflora and the gut immune system are critical for establishing a proper balance between immune host defense mechanisms and tissue health. Changes in gut bacteria composition described as "disbiosis" have been associated with intestinal inflammation and metabolic syndrome. The vast majority of studies on the interaction between commensal microbiota and the host have focused on gut bacteria, and the terms "intestinal microbiota" and "intestinal bacteria" are often used interchangeably. However, recent studies have begun to note that a fraction of mucosa-associated microorganisms are not bacterial. For example, commensal viruses can trigger gut inflammation by targeting host Paneth cells or indirectly by targeting commensal bacteria. Although a few studies have suggested the presence of commensal fungi in the gut, it is unknown whether they interact with the mucosal immune system or influence disease. As illustrated recently by Segmented Filamentous Bacteria (SFB) and *Clostridium* sp., even organisms representing a proportionally small fraction of the total microbiome can have profound effects on the host immune system. Thus it is important to evaluate whether gut fungi significantly influence the maintenance of host intestinal homeostasis.

Fungi are recognized by a number of immune receptors among which Dectin-1 has emerged as key for recognition, phagocytosis, and killing by myeloid phagocytes. Dectin-1 is a C-type lectin receptor that recognizes β-1,3-glucans found in the cell walls of nearly all fungi. Dectin-1 activates intracellular signals through CARD9 leading to inflammatory cytokine production and enhanced induction of Th17 immune responses. Deficiencies in either Dectin-1 or CARD9 result in enhanced susceptibility to pathogenic fungal infections in humans and mice. Polymorphic variants in the gene for CARD9 are strongly associated with Crohn's disease and ulcerative colitis in humans. Furthermore, anti-*Saccharomyces cerevisiae* antibodies (ASCA) against yeast mannan have been strongly associated with Crohn's disease. Together, these later findings suggest a possible link between immune responses to commensal fungi and intestinal disease.

SUMMARY OF THE INVENTION

Various embodiments include a method of treating an inflammatory bowel disease (IBD) in a subject, comprising providing a composition of a gut fungi, and administering a therapeutically effective dosage of the composition to the subject. In another embodiment, the IBD is ulcerative colitis. In another embodiment, the gut fungi is *saccharomycopsis*. In another embodiment, the gut fungi is *saccharomycopsis fibuligera*. In another embodiment, the subject is human. In another embodiment, the subject is a rodent. In another embodiment, the IBD is a severe form of ulcerative colitis. In another embodiment, the composition of a gut fungi is a probiotic biotherapy.

Other embodiments include a method of diagnosing susceptibility to a disease in a subject, comprising obtaining a sample from the individual, subjecting the sample to a genotyping assay adapted to determine the presence or absence of one or more risk variants at the Dectin-1 gene (CLEC7A), and diagnosing susceptibility to the disease in the individual based on the presence of one or more risk variants at the Dectin-1 gene (CLEC7A). In another embodiment, the disease is an inflammatory disease. In another embodiment, the disease is inflammatory bowel disease (IBD). In another embodiment, the disease is a severe form of ulcerative colitis. In another embodiment, the disease is based on the inability to control fungi in the gut of the individual.

Other embodiments include a method of diagnosing a disease in a subject, comprising obtaining a sample from the gut of the subject, assaying the sample to determine a composition of gut fungi strain, diagnosing the disease based on the composition of gut fungi strain in the subject. In another embodiment, the composition of gut fungi strain comprises *saccharomycopsis fibuligera*. In another embodiment, the *saccharomycopsis fibuligera* is characterized by an absence of functioning Dectin-1. In another embodiment, the subject is human. In another embodiment, the disease is a severe form of ulcerative colitis. In another embodiment, the disease is an inflammatory disease.

Various embodiments include a probiotic, comprising a composition of gut fungi comprising *saccharomycopsis*. In another embodiment, the composition comprises *saccharomycopsis fibuligera*.

Other embodiments include a method of treating a disease in a subject, comprising diagnosing a disease based on a composition of gut fungi strain present in the subject, and treating the subject. In another embodiment, treating the subject comprises administering a probiotic biotherapy. In another embodiment, the disease is inflammatory bowel disease (IBD).

Other features and advantages of the invention will become apparent from the following detailed description, taken in conjunction with the accompanying drawings, which illustrate, by way of example, various embodiments of the invention.

BRIEF DESCRIPTION OF THE FIGURES

FIG. 25 depicts, in accordance with an embodiment herein, a table of CLEC7A risk haplotype analysis of MRUC and Non-MRUC patients.

FIG. 26 depicts, in accordance with an embodiment herein, a table of CLEC7A risk haplotype analysis of MRUC and Non-MRUC patients compared to healthy controls.

DESCRIPTION OF THE INVENTION

Figure 1:
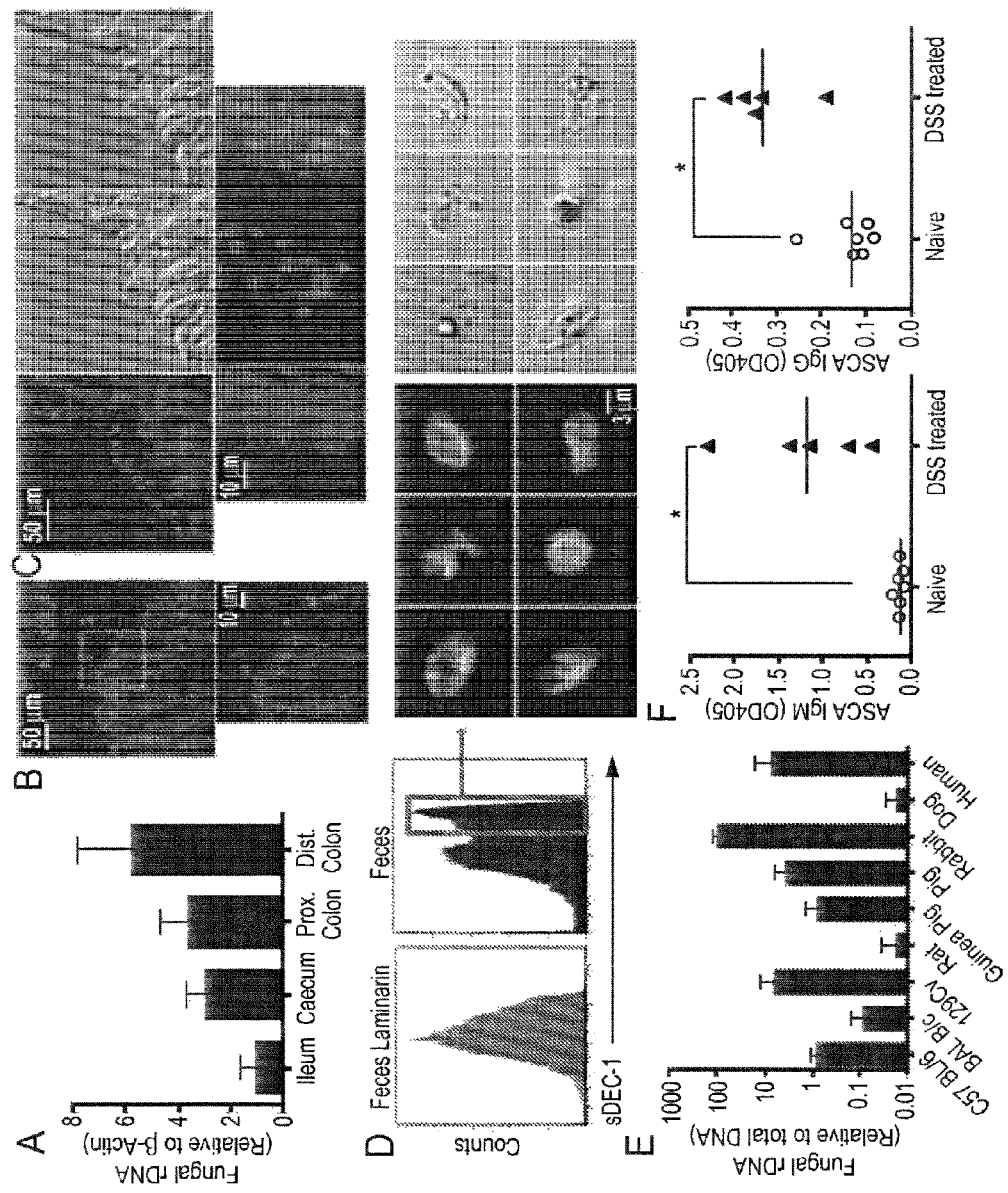
FIG. 1 depicts, in accordance with an embodiment herein, commensal fungi are present in the intestine and are recognized by Dectin-1. (A) Prevalence of fungi in mucosa isolated from ileum, caecum, proximal (prox) and distal (dist) colon of C57BL/6J mice. ITS1-2 rDNA level was analyzed by qPCR and normalized to β-actin DNA. (B), (C) Visualization of commensal fungi in the intestine. Colon sections were stained with (B) anti-fungal antibody or with (C) a soluble Dectin-1 probe (sDEC-1) and counterstained with DAPI. Lower panels in (C) show that DAPI-stained bacteria and fungi are in close proximity to each other. (D) Intestinal fungi are recognized by Dectin-1. Fecal pellets were homogenized and labeled with sDEC-1 in presence (gray histogram) or absence (black histogram) of laminarin (a soluble β-glucan) to block specific binding. Binding was assessed by flow cytometry (left panels). Dectin-1-binding fungi were sorted (right panels) and visualized by confocal microscopy. (E) Intestinal fungi are present in the gut of different mammals. Feces were analyzed for fungal 18S rDNA by qPCR. (F) ASCA generation after DSS colitis. Mice were exposed twice to 2.5% DSS-supplemented water for 7 days each separated by two weeks of recovery. Serum samples were collected before DSS treatment (day 0) and 2 weeks after the last DSS cycle (42 days total) and ASCA IgM and IgG were measured by ELISA. Each symbol represents a mouse, all error bars indicate the s.d. *$P<0.05$; unpaired t test. All data are representative of at least two independent experiments with similar results.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"IBD" as used herein is an abbreviation of inflammatory bowel disease.

"CD" as used herein is an abbreviation of Crohn's Disease.

"SNP" as used herein is an abbreviation of single nucleotide polymorphism.

As used herein, the term "biological sample" means any biological material from which nucleic acid molecules can be prepared. As non-limiting examples, the term material encompasses whole blood, plasma, saliva, check swab, or other bodily fluid or tissue that contains nucleic acid.

As disclosed herein, the intestinal microflora typically equated with bacteria, influences diseases such as obesity and inflammatory bowel disease (IBD). Here, the inventors demonstrate that the mammalian gut contains a rich fungal community that interacts with the immune system through the innate immune receptor Dectin-1. Mice lacking Dectin-1 are susceptible to chemically-induced colitis and show elevated Th1 and Th17 mucosal immune responses. Disease susceptibility was due to altered responses to indigenous fungi. In humans, the inventors identified a polymorphism in the gene for Dectin-1 (CLEC7A) that is strongly linked to a severe form of ulcerative colitis. Together the inventors' findings reveal a novel eukaryotic fungal community in the gut that coexists with bacteria and significantly expands the repertoire of organisms interacting with the intestinal immune system to influence health and disease.

In one embodiment, the present invention provides a method of diagnosing susceptibility to inflammatory bowel disease in an individual, comprising obtaining a sample from the individual, assaying the sample to determine the presence or absence of one or more risk variants at the Dectin-1 gene (CLEC7A), and diagnosing susceptibility to inflammatory bowel disease in the individual based on the presence of one or more risk variants at the Dectin-1 gene (CLEC7A). In another embodiment, the inflammatory bowel disease is a severe form of ulcerative colitis. In another embodiment, the present invention provides a method of diagnosing susceptibility to a severe form of ulcerative colitis based on the inability to control fungi in the gut of the individual.

In another embodiment, the present invention provides a method of diagnosing colitis and/or a disease mediated by an elevated Th1 and/or Th17 mucosal immune response in an individual, comprising obtaining a sample from the individual, assaying the sample to determine the presence or absence of functioning Dectin-1 relative to a normal subject, and diagnosing colitis and/or a disease mediated by an elevated Th1 and/or Th17 mucosal immune response based on the absence of functioning Dectin-1 relative to a normal subject. In another embodiment, an absence of functioning Dectin-1 is characterized by a deficiency of Dectin-1 in the individual.

In another embodiment, the present invention provides a method of treating inflammatory bowel disease in an individual, comprising obtaining a sample from the individual, assaying the sample to determine a deficiency of Dectin-1 in the individual, and treating the individual.

Beneficial commensal bacteria called "probiotic bacteria" have been utilized for treatment of diseases and have been developed into a profitable industry bringing large revenue. As disclosed herein, fungal microbiome (mycobiome) interacts with the host mucosal immune system and with the bacterial gut microbiome to influence disease. The inventors found that certain species of commensal fungi are able to induce protective mechanisms that ameliorate intestinal inflammation and colitis. Mice supplemented with *Saccharomycopsis fibuligera*, a commensal fungus isolated from murine gut, showed decreased gut inflammation and milder intestinal disease in an experimental model of colitis). It worth noting that *Saccharomycopsis fibuligera* has been used in rice wine production for centuries, but its probiotic properties have not been investigated. Other commensal fungi isolated from mouse or human gut would display similar probiotic properties. In one embodiment, probiotic fungi can be used as a tool for prophylactic and treatment of intestinal disorders, obesity, metabolic syndrome and colon cancer.

Furthermore, in another embodiment, mycobiome may be used as a diagnostic marker. Changes in the composition of the gut bacterial microbiome described as "dysbiosis" have been associated with intestinal inflammation and metabolic syndrome. Increased representation of gut bacteria belonging to Prevotellaceae and TM7 phyla can be linked to diseases such as IBD, obesity and metabolic syndrome. Specific changes to bacterial microbiome can be used as a marker of a disease and that the bacterial microbiome can be actually used as a diagnostic tool in number of diseases such as IBD, obesity and metabolic syndrome. As disclosed herein, microbiome is a dynamic structure which changes during inflammation and according to the disease state. The inventors found that certain fungal genera (*Candida, Trichosporon*) known as opportunistic pathogens expand according to disease severity whereas the relative abundance of probiotic fungal genera (such as *Saccharomyces* and *Saccharomycopsis*) decreases (see the attached manuscript). In one embodiment, the present invention provides for methods of diagnosing a disease, where changes in the gut mycobiome can be used as a diagnostic marker for a disease state and severity. In another embodiment, the disease is IBD, obesity, metabolic syndrome and/or cancer.

In another embodiment, the present invention provides a method of treatment, where gut mycobiome may be altered using targeted antifungal therapy as a tool for treatment. Studies of the bacterial microbiome have additionally shown that targeted antibiotic therapy can be beneficial in treatment of IBD, obesity, metabolic syndrome, colon cancer and neurological disorders. The inventors showed that certain species of gut commensal fungi can be protective whereas other fungal species can be pathogenic during certain conditions and can lead to exacerbated disease. As disclosed herein, the inventors demonstrated that certain commensal fungi known as opportunistic pathogens (*Candida* and *Trichosporon* species) can contribute to development of intestinal inflammation in which case antifungal therapy targeting these specific species can be used as a mean of treatment. In one embodiment, targeted anti-fungal therapy can be used for treatment of forms of IBD, obesity, metabolic syndrome and colon cancer. In another embodiment, the gut mycobiome may influence gut bacterial microbiome, a property used as a treatment protocol itself.

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature," Nucleic Acids Research 28:655-661 (2000)). Minor grove binders include, but are not limited to, compounds such as dihydrocyclopyrroloindole tripeptide (DPI).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press. Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against CD in an individual may be practiced using one or any combination of the well known assays described above or another art-recognized genetic assay.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

The intestinal microflora, typically equated with bacteria, influences diseases such as obesity and inflammatory bowel disease (IBD). Here the inventors show that the mammalian gut contains a rich fungal community that interacts with the immune system through the innate immune receptor Dectin-1. Mice lacking Dectin-1 are susceptible to chemically-induced colitis and show elevated Th1 and Th17 mucosal immune responses. Disease susceptibility was due to altered responses to indigenous fungi. In humans we identified a polymorphism in the gene for Dectin-1 (CLEC7A) that is strongly linked to a severe form of ulcerative colitis. Together our findings reveal a novel eukaryotic fungal community in the gut that coexists with bacteria and significantly expands the repertoire of organisms interacting with the intestinal immune system to influence health and disease.

Mucosal fungal infections are relatively common in Crohn's Disease patients, and antibodies against fungal antigens (ASCA) are a well accepted clinical marker for disease severity. However what fungi populate the intestine and how immunity to them might play a role in inflammatory disease is currently unknown. Fungi are sensed by number of innate immune receptors among which Dectin-1, expressed on myeloid cells, is critical for host defense. The inventors found that commensal fungi populate the murine gut and that Dectin-1$^{-/-}$ mice are more susceptible to experimental colitis characterized by increased infiltration of Th17 and Th1 cells in the colon. Interestingly this pathology was driven by intestinal fungi, and antifungal therapy ameliorated colitis severity in Dectin-1$^{-/-}$ mice. Deep sequencing analysis of the fungal microbiome in murine feces revealed fungal species that are overrepresented in the gut during colitis. Mice supplemented with a specific commensal fungus experienced more severe colitis and augmented Th17 mucosal responses in absence of Dectin-1, while another commensal fungus enhanced Th17 responses in Dectin-1$^{-/-}$ mice but did not further affect the intestinal pathology. The data demonstrate that altered interactions between the fungal microflora and the host mucosal immune system can profoundly influence intestinal pathology.

Example 2

Commensal Fungi and Dectin-1 Interactions

Figure 5:
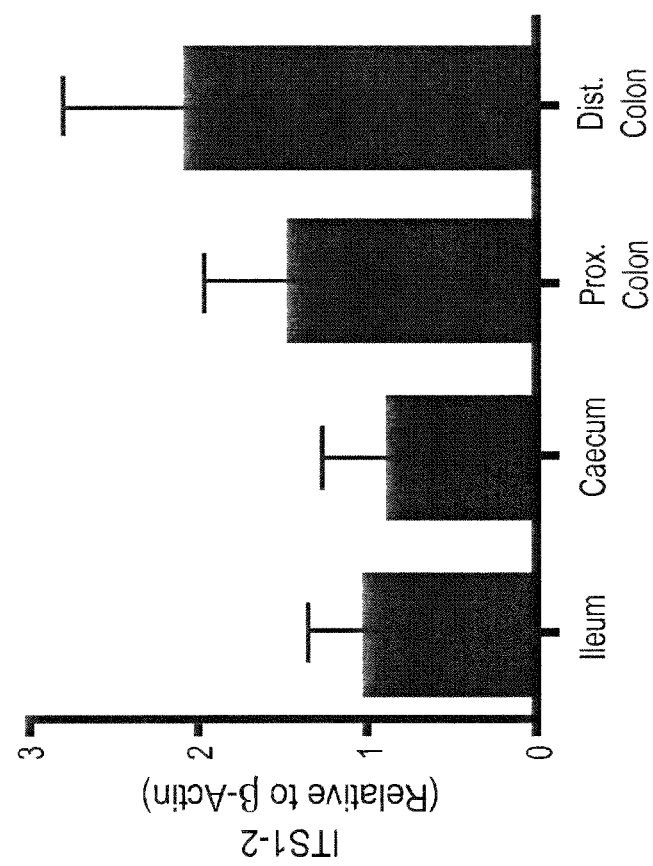
FIG. 5 depicts, in accordance with an embodiment herein, commensal fungi are present in the intestine of 129S2/Sv mice.
(A) Mucosa was isolated from ileum, caecum, proximal and distal colon of 129S2/Sv mice; ITS1-2 rDNA level was analyzed by qPCR and normalized to β-actin DNA.
Figure 6:
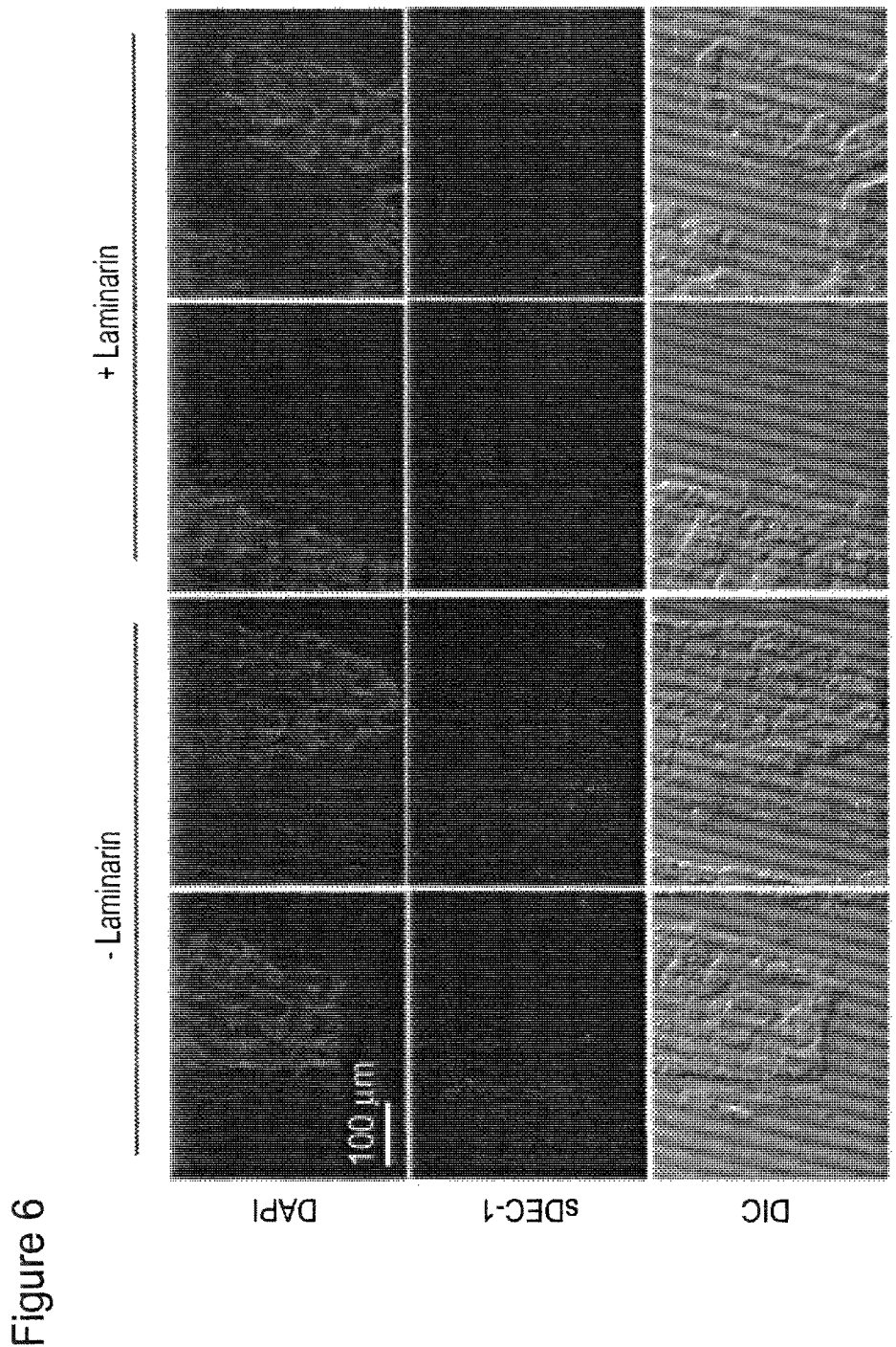
FIG. 6 depicts, in accordance with an embodiment herein, soluble β-glucan blocks binding of Dectin-1 to intestinal fungi. Colon sections were stained with a soluble Dectin-1 probe (sDEC-1) in the presence or absence of soluble β-glucan (laminarin) and counterstained with DAPI. The soluble Dectin-1 probe (red) binds to abundant luminal fungi, and this interaction is completely blocked by soluble glucan, indicating that the probe is specific.

The inventors examined the distribution of fungi in the murine gastrointestinal tract and detected fungal rDNA throughout the intestines with highest densities in the terminal colon of C57BL/6 (FIG. 1A) and 129S2/Sv (FIG. 5) mice. They stained colonic tissue sections and observed that fungi are abundant and in close proximity with commensal bacteria (FIGS. B and C and FIGS. 6 to 8). Furthermore, the inventors found that a soluble Dectin-1 probe binds to 5 to 7% of the fecal material consisting of fungal cells with various morphologies (FIG. 1D). Fungi were also present in rat, guinea pig, rabbit, pig, dog, and human feces (FIG. 1E). Together the data demonstrate that commensal fungi contribute to the intestinal microbial community in many species.

Figure 2:
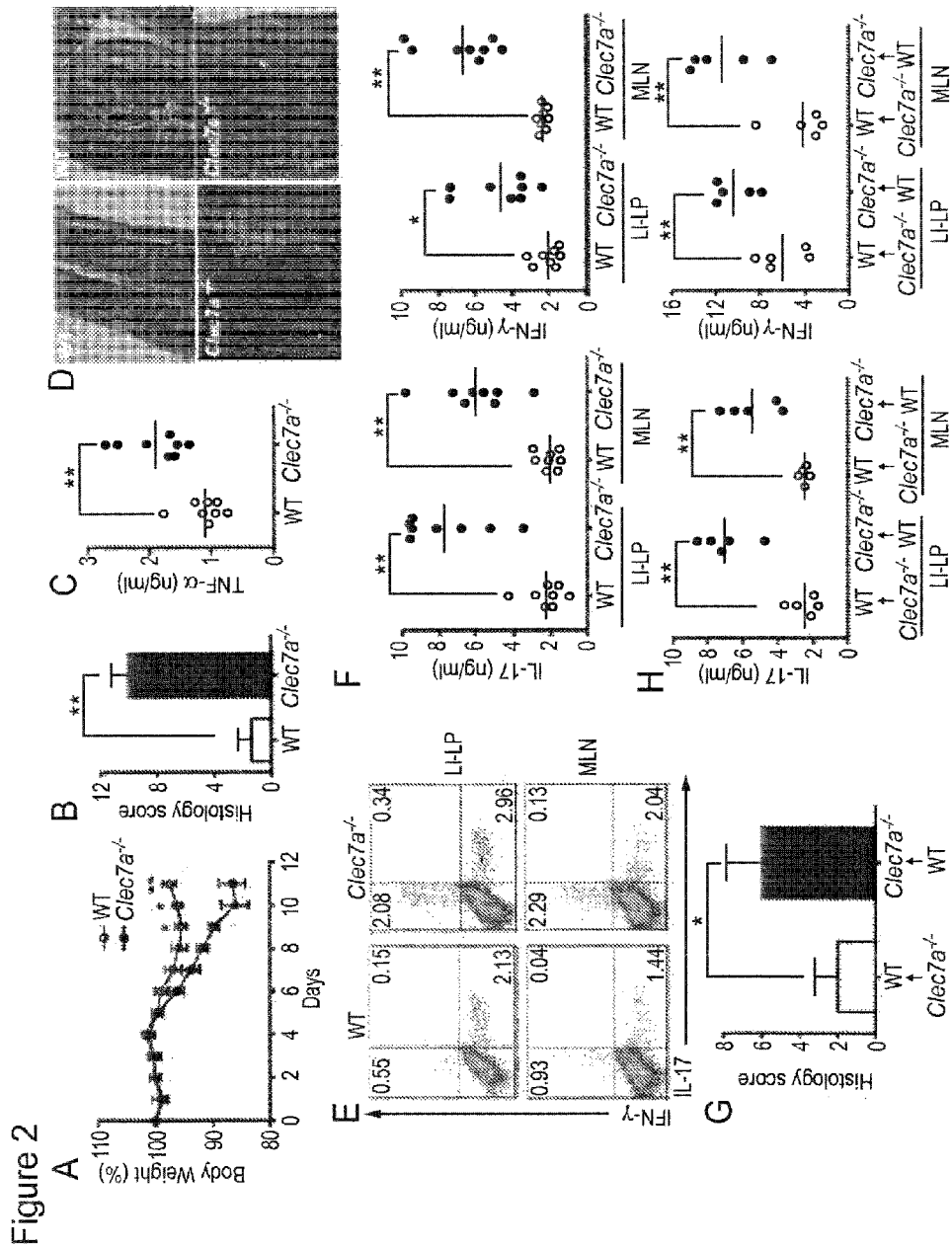
FIG. 2 depicts, in accordance with an embodiment herein, dectin-1 regulates severity of colitis. Wild type (WT) and Clec7a-/- littermates were treated with 2.5% DSS for 7 days and kept on water for 4 additional days. Colitis progress and severity were assessed by measuring body weight during treatment (A) and histology (B, D), and TNF-α production in the colon (C) on day 11. (E) Dot plots show the percentage of IL-17 and IFN-γ producing CD4+ T cells isolated from large intestine lamina propria (LI-LP) and mesenteric lymph nodes (MLN) on day 11. (F) LI-LP and MLN cells were cultured with antibodies against CD3 and CD28. The production of IL-17 and IFN-γ was measured by ELISA. Microbiota from Clec7a-/- mice do not transfer disease to the WT. (G), (H) WT and Clec7a-/- mice were given an antibiotic cocktail for 3 weeks, transplanted as indicated (red) with fecal microflora from WT or Clec7a-/- mice and treated with DSS as in (A). Disease severity was accessed by histology score (G) and by cytokine production by anti-CD3/anti-CD28 stimulated LI-LP and MLN T cells (H). Each symbol represents a different mouse. One of four independent experiments is shown. Error bars, s.d., *$P<0.05$, **$P<0.01$
Figure 10:
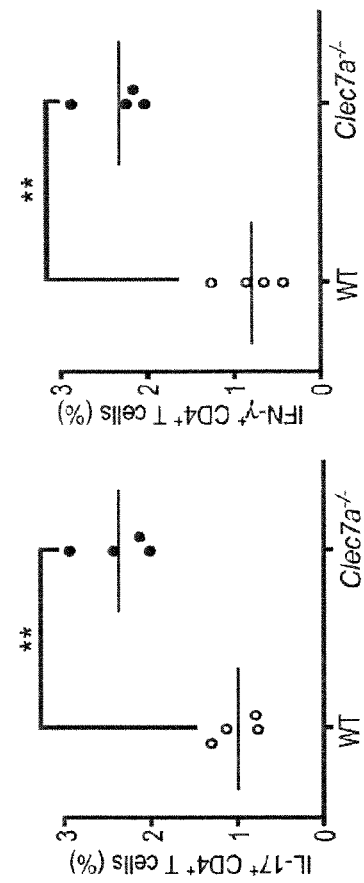
FIG. 10 depicts, in accordance with an embodiment herein, enhanced frequency of IL-17 and IFN-γ producing CD4-T cells in the intestines of Clec7a–/– mice after DSS. WT and Clec7a–/– mice were treated with 2.5% DSS for 7 days and kept on water for 4 additional days. LI-LP cells were isolated and stimulated in vitro with PMA, ionomycin and Brefeldin A. Cells were permeabilized and stained with anti-CD4, anti-IL-17 and anti-IFN-γ antibodies. Samples were analyzed using FACS. Graphs represent the frequency of IL-17+ and IFN-γ+ cells inside the CD4+ T cell population. Each symbol represents a different mouse. **$P<0.01$. Data are from one experiment representative of three.
Figure 11:
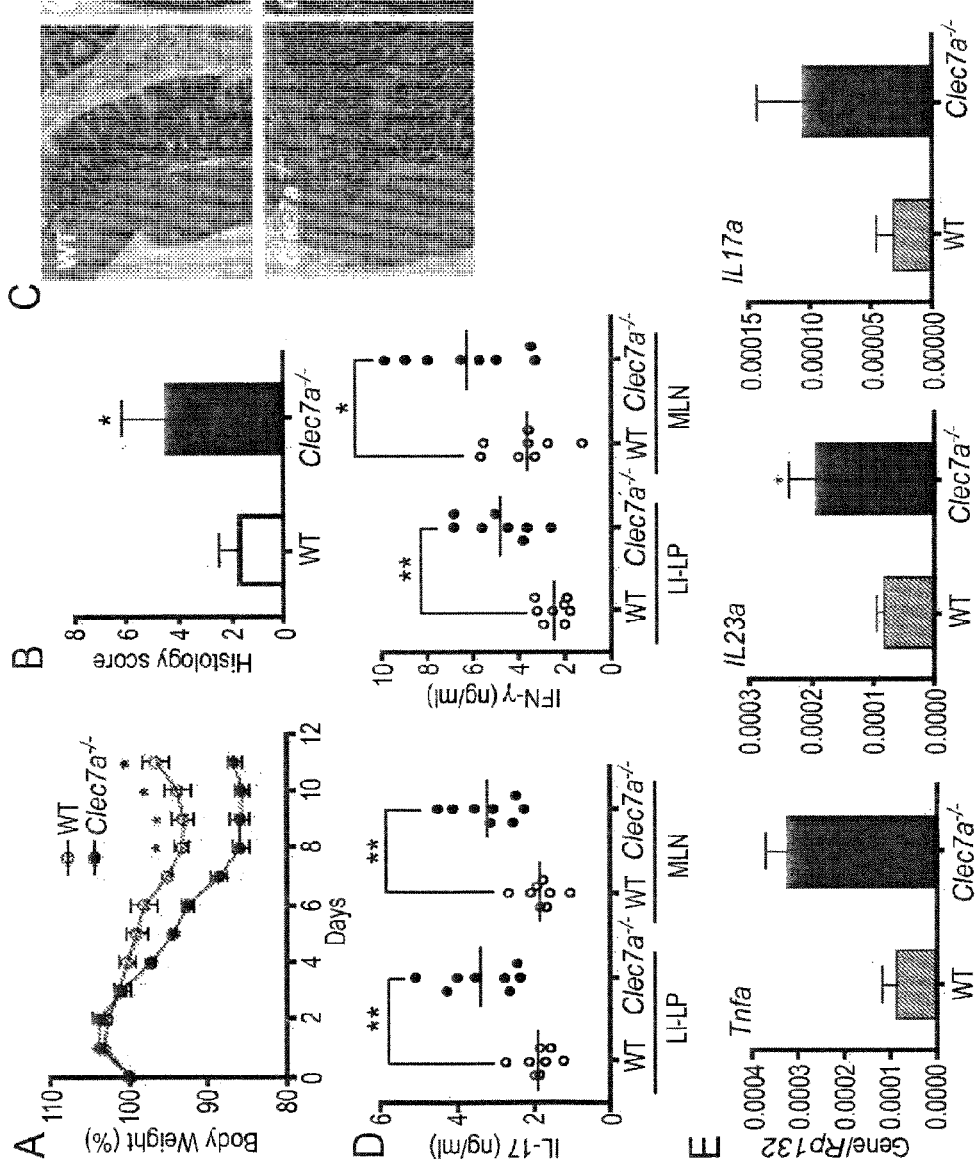
FIG. 11 depicts, in accordance with an embodiment herein, dectin-1 regulates severity of colitis. (A) Body weight in co-housed wild type (WT) and Clec7a–/– mice treated with 2.5% DSS for 7 days and kept on water for 4 additional days. Histology score (B) on haematoxylin and eosin stained colon sections (C) was determined on day 11. (D) LI-LP and MLN cells were cultured with antibodies against CD3 and CD28. The production of IL-17 and IFN-γ was measured by ELISA. (E) The expression of tnfa (TNF-α), 1123a (IL-23p19) and Il17a (IL-17A) in colons of WT and Clec7a–/– mice 4 days after DSS treatment was measured by qPCR and normalized to Rpl32 mRNA. Each symbol represents a different mouse. One of four independent experiments is shown. Error bars, s.d., *$P<0.05$, **$P<0.01$.
Figure 12:
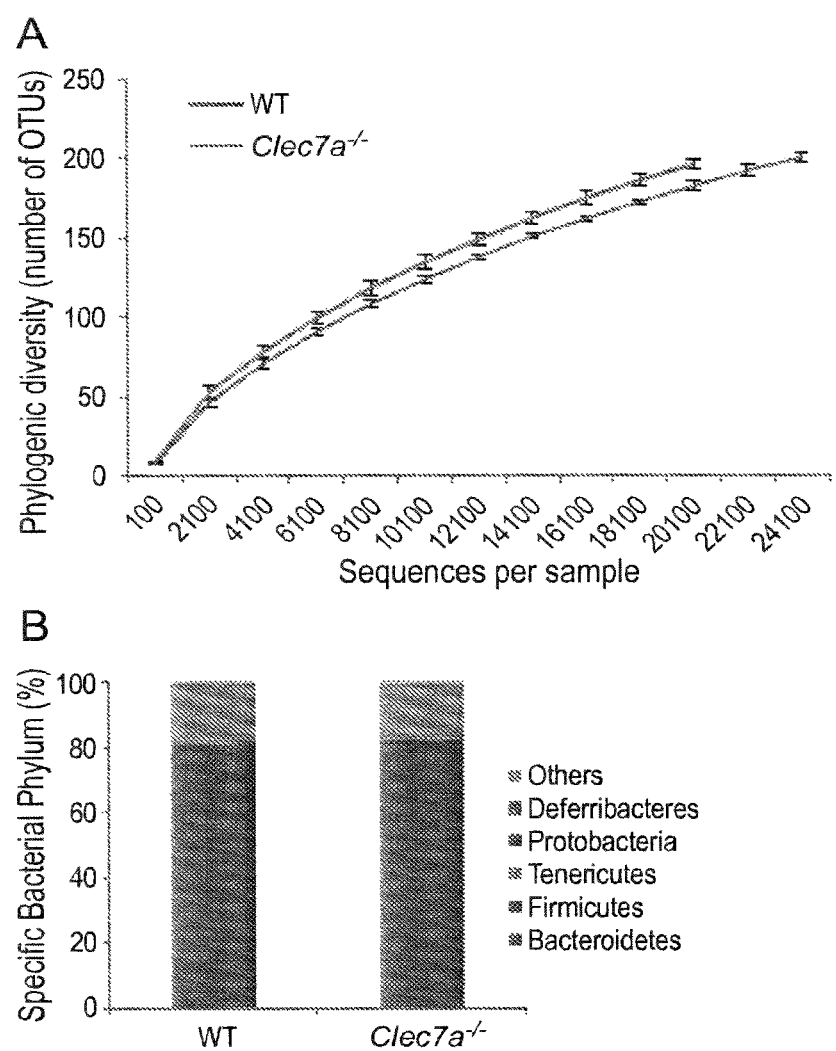
FIG. 12 depicts, in accordance with an embodiment herein, bacterial phyla analysis of feces from WT and Clec7a–/– mice. DNA was isolated from feces of WT and Clec7a–/– littermates (n=5) and subjected to Illumina GA sequencing. (A) Rarefaction curve of phylogenic diversity in fecal samples from WT and Clec7a–/– mice. The curve depicts the number of operational taxonomic units (OTU) observed at different sampling depths where the X axis is the number of reads in the V2/V3 region and the Y axis is the number of OTUs observed. (B) Quantitative analysis of the major bacterial phyla in wild type and Clec7a–/– mice. Illumina GA data were analyzed and presented as relative percentage of dominant bacterial phyla.
Figure 13:
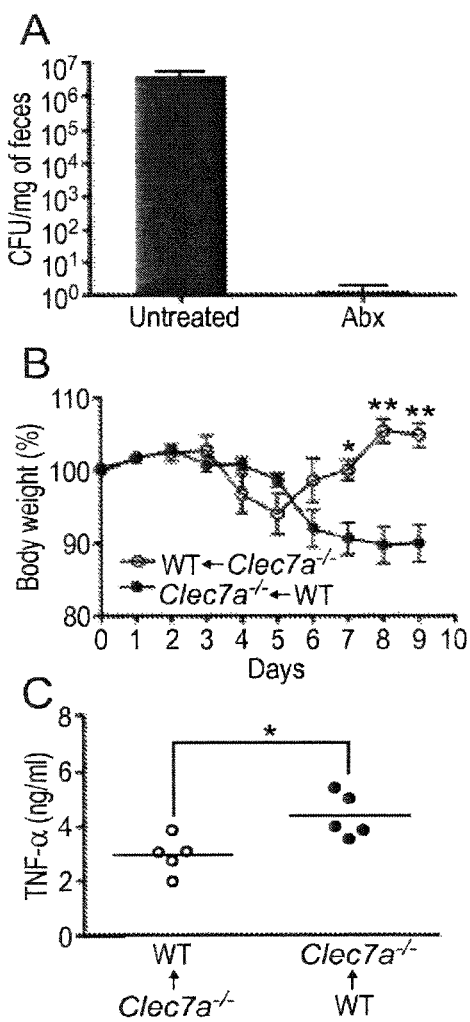
FIG. 13 depicts, in accordance with an embodiment herein, fecal transplant does not rescue Clec7a–/– mice. WT and Clec7a–/– mice were given an antibiotic cocktail for 3 weeks, transplanted as indicated (red) with fecal microflora from WT or Clec7a–/– mice and treated with 2.5% DSS for 7 days. (A) To access microflora depletion, feces were collected and plated before and after antibiotic treatment (n=10). (B) Colitis progression and severity were assessed by measuring body weight during treatment, and (C) TNF-α production in the colon on day 11. Each symbol represents a different mouse. One of two independent experiments is shown. Error bars, s.d., *$P<0.05$, **$P<0.01$.
Figure 14:
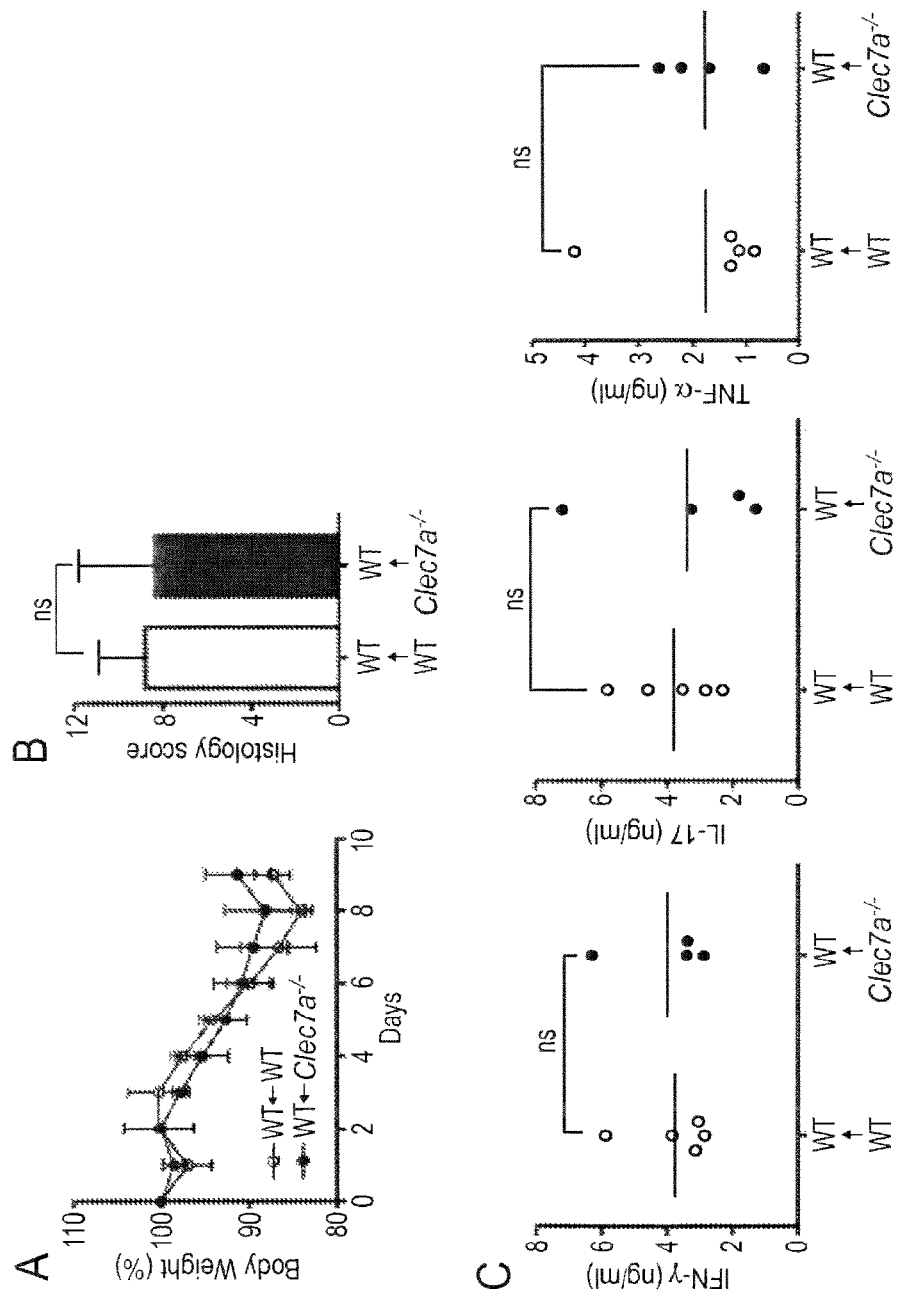
FIG. 14 depicts, in accordance with an embodiment herein, fecal microflora from Clec7a–/– mice does not transfer susceptibility to colitis in WT mice. WT mice were given an antibiotic cocktail for 3 weeks, transplanted as indicated (red) with fecal microflora from WT or Clec7a–/– mice and treated with 2.5% DSS for 7 days. (A) Body weight was measured daily. Histology score (B), and production of IL-17 and IFN-γ by LI-LP, and TNF-α production in the colon (C) were determined on day 11. Each symbol represents a different mouse. One of two independent experiments is shown. Error bars, s.d., *$P<0.05$. **$P<0.01$.
Figure 15:
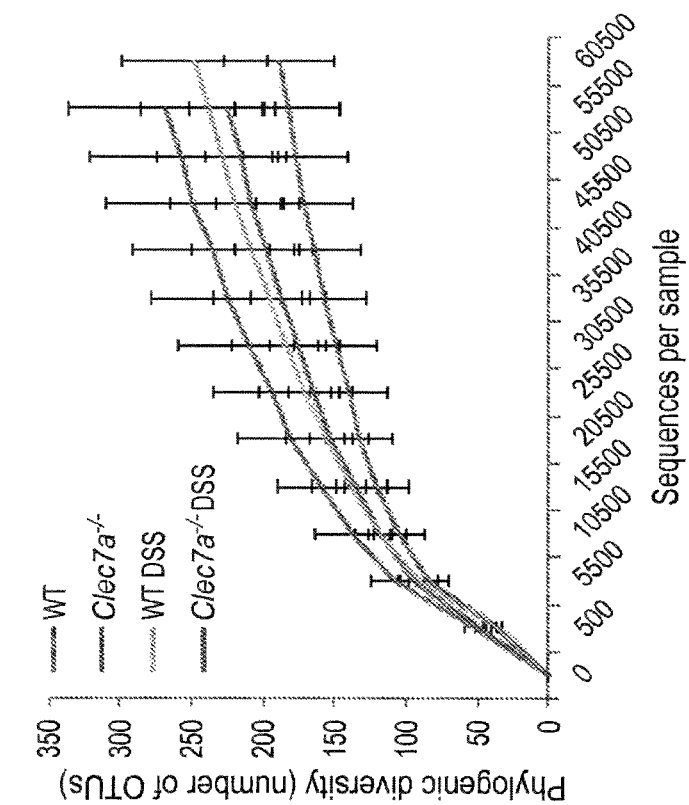
FIG. 15 depicts, in accordance with an embodiment herein, rarefaction curve demonstrating fungal sequence coverage in WT and Clec7a–/– mice before and after colitis. DNA was isolated from feces of WT and Clec7a–/– mice before and after the onset of colitis (n=16) and subjected to Illumina GA sequencing. The curve depicts the number of operational taxonomic units (OTU) observed at different sampling depth where the X axis is the number of ITS1-2 reads and the Y axis is the number of OTUs observed.
Figure 16:
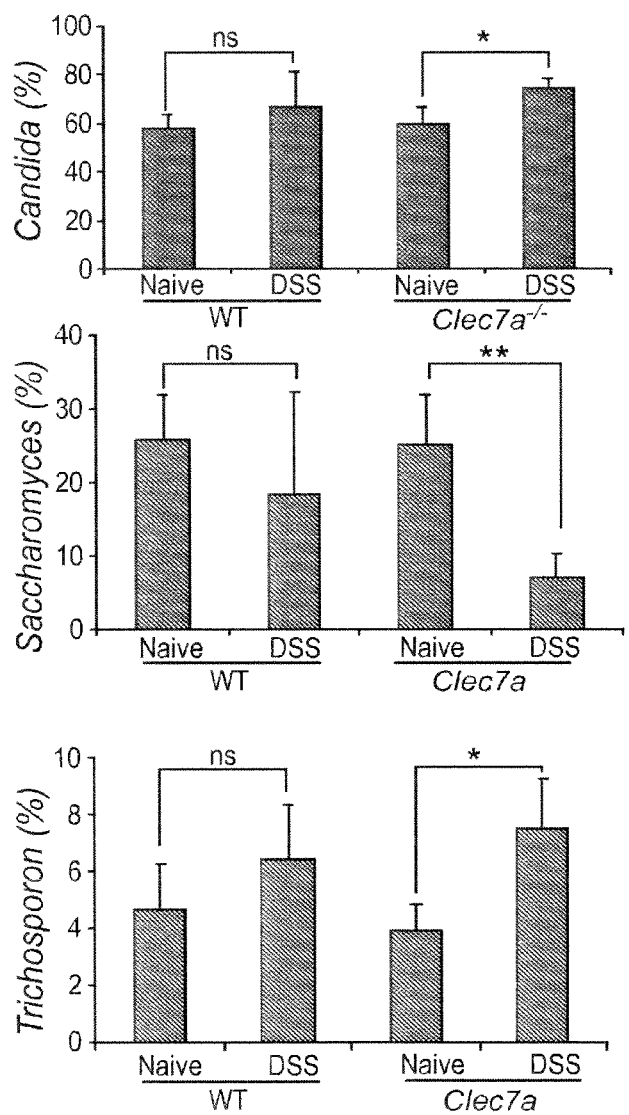
FIG. 16 depicts, in accordance with an embodiment herein, Clec7a–/– show changes in the distribution of major fungal genera during colitis. Quantitative analysis of the three major intestinal fungal genera in wild type and Clec7a–/– mice before and after treatment with DSS was performed. Illumina GA data were analyzed and presented as relative percentage of dominant fungal genera (n=16 mice). Error bars, s.d., *$P<0.05$, **$P<0.01$.

The inventors also examined whether gut fungi can be detected by the immune system upon intestinal insult when barrier integrity is compromised. They utilized a mouse model of dextran sodium sulfate (DSS)-induced colitis extended to allow antibody responses to develop. They found that DSS-induced intestinal inflammation led to the development of circulating IgM and IgG antibodies to fungi (ASCA) (FIG. 1F), suggesting that fungal antigens indigenous to the gut might be responsible for the induction of ASCA during colitis. Since they found that gut commensal fungi are recognized by Dectin-1, we tested whether Dectin-1-deficient mice (Clec7a−/−) are susceptible to DSS-induced colitis. Clec7a−/− mice experienced increased weight loss (FIG. 2A) and displayed altered histology characterized by increased mucosal erosion, crypt destruction, inflammatory cell infiltration, and TNF-α production in the colon (FIG. 2B to D) as compared to their wild type (WT) littermate controls. They detected augmented production of IFN-γ and IL-17 in mesenteric lymph nodes (MLNs) and colons from Clec7a−/− mice (FIGS. 2E and F) which correlated with higher frequencies of inflammatory Th1 and Th17 cells (FIG. 2E and FIG. 10). Identical results were obtained comparing co-housed Clec7a−/− and WT mice. These results indicate that Dectin-1 deficiency leads to increased susceptibility to colitis. Since many studies have documented the importance of bacteria in intestinal inflammation, we examined whether differences in bacteria could contribute to the susceptible phenotype of Dectin-1-deficient mice. They observed no significant differences in major phyla of commensal bacteria between WT and Clec7a−/− mice. To directly determine whether microflora can transfer disease, the inventors depleted intestinal bacteria and fungi with antibiotics transplanted with fecal microflora from WT or Clec7a−/− mice, and exposed mice to DSS. Fecal microflora from Clec7a−/− mice did not transfer susceptibility to disease (FIGS. 2G and H).

Figure 3:
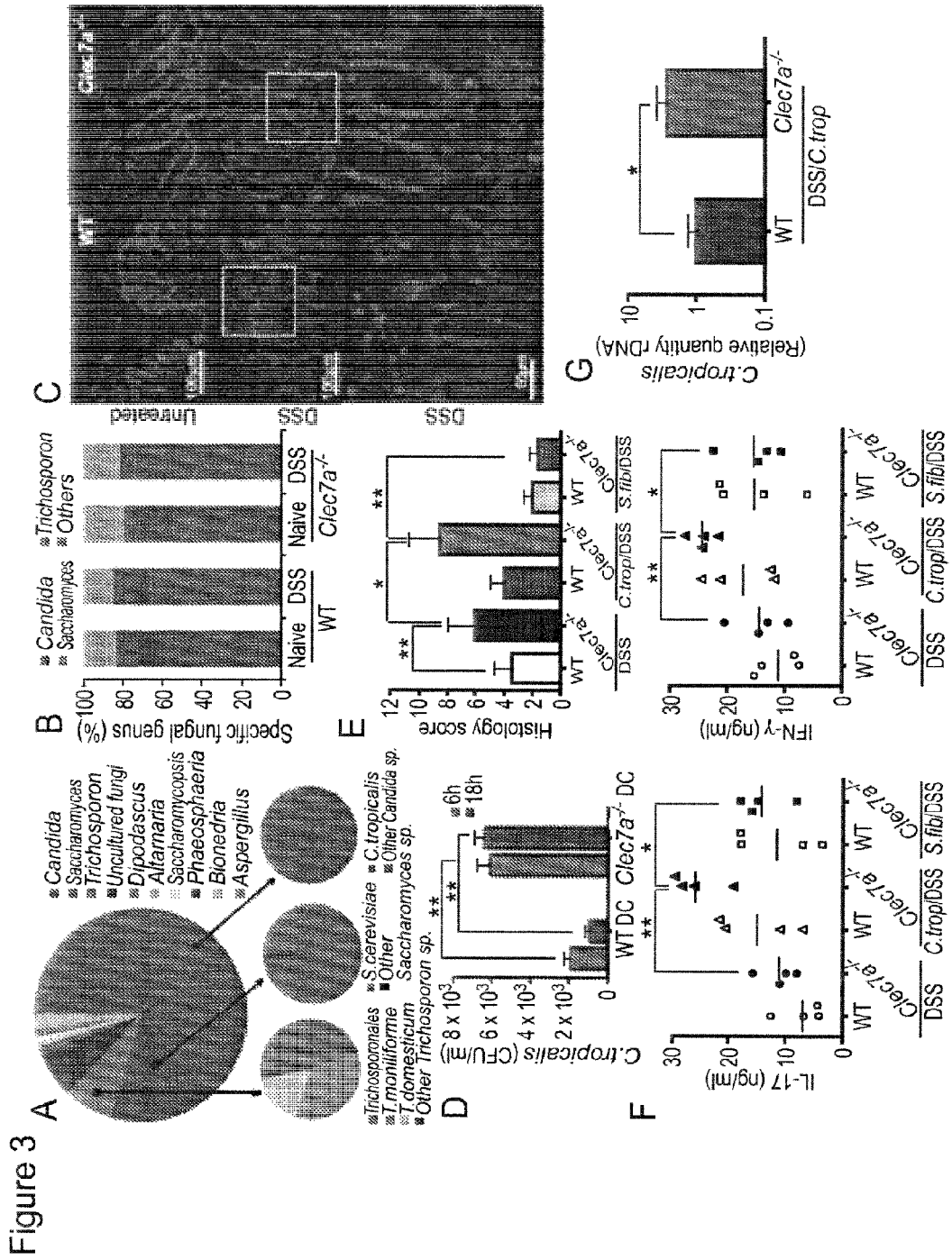
FIG. 3 depicts, in accordance with an embodiment herein, defining the fungal microbiome and characterizing the specific role of Dectin-1-mediated host defense during colitis (A) DNA was isolated from murine feces and fungal microbiome analysis was performed using Roche 454 and Illumina GA sequencing of ITS1-2 rDNA. The taxonomic distribution of the most abundant fungal genera is shown (large pie chart), and species breakdown for major groups are provided (small pie charts). (B) Quantitative analysis of the major intestinal fungal genera in wild type and Clec7a-/- mice before and after treatment with DSS. Illumina GA data were analyzed and presented as relative percentage of dominant fungal genera (n=16 mice). (C) Fungal invasion of colonic tissue in Clec7a-/- mice during colitis. Colon sections from WT and Clec7a-/- mice before and after colitis were stained with the sDEC-1 probe and counterstained with DAPI. (D) Reduced anti-fungal killing activity by intestinally conditioned Clec7a-/- dendritic cells. Intestinally conditioned dendritic cells were incubated with live C. tropicalis and killing was assessed after 6 and 18 hours. (E, F, G) WT and Clec7a-/- mice were supplemented with four doses of C. tropicalis or S. fibuligera every other day, and then treated with 2.5% DSS for 7 days and kept on water for 4 additional days. Histology score (E) and the production of IL-17 and IFN-γ by MLN cells (F) were determined 4 days after DSS treatment. (G) The presence of C. tropicalis was analyzed by qPCR after DSS treatment. Data are representative of at least two independent experiments with similar results. Error bars, s.d., *$P<0.05$, **$P<0.01$.

There is very little known about what commensal fungi populate the murine gut or how they might contribute to colitis in Dectin-1 deficient mice. To define the mouse intestinal fungal microbiome DNA was isolated from murine intestinal luminal content, and the internal transcribed spacer region (ITS1-2) of fungal rDNA was amplified and subjected to highthroughput sequencing. Combining data from 23 mice analyzed, we obtained over 30 Mb of raw data from 454 pyrosequencing and over 2.2 GB of raw data from Illumina GA sequencing together containing over 1.3 million individual sequences which passed quality control. Detailed analysis identified over 100 different well-annotated fungal species representing at least 50 genera illustrating the fungal diversity. In addition, over 100 novel/unannotated fungi were identified representing the large uncharacterized nature of the fungal biome in the gut. Interestingly, 97.3% of all the fungal sequences identified, belonged to 10 fungal species with 65.2% of the sequences belonging to a single fungus: *Candida tropicalis* (FIG. 3A). The inventors also examined mouse food, and found that 7 of the 20 most commonly represented fungi found in the gut were present in the mouse food, but these species ultimately accounted for only 1.5% of the fungi in the intestines (FIG. 17, 18), suggesting that highly represented fungal species are indigenous to the gut and are not delivered with the food.

Figure 17:
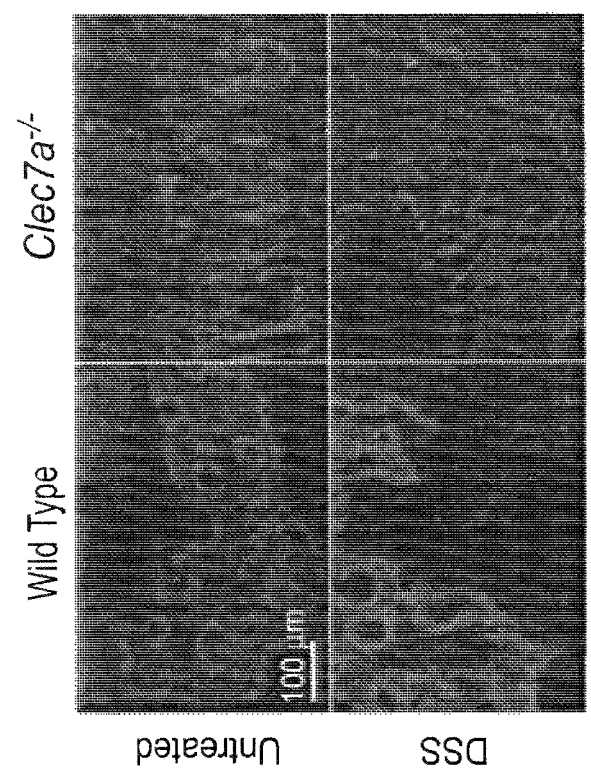
FIG. 17 depicts, in accordance with an embodiment herein, fungi penetrate the colon of Clec7a–/– mice during colitis. Colon sections from WT and Clec7a–/– mice before and after colitis were stained with the sDEC-1 probe and counterstained with DAPI.
Figure 18:
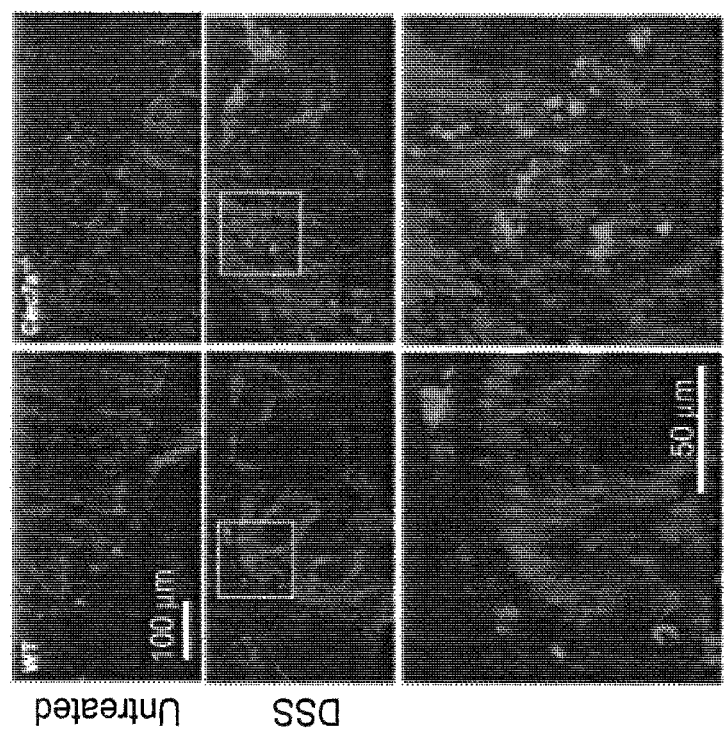
FIG. 18 depicts, in accordance with an embodiment herein, fungal invasion of colonic tissue in Clec7a–/– mice during colitis. Colon sections from WT and Clec7a–/– mice before and after colitis were stained with the antifungal antibody and counterstained with DAPI.

Studies have shown that intestinal inflammation can lead to changes in commensal bacterial communities that affect the host. One study has reported increased fungal burden in intestines of Crohn's Disease patients, and another has shown increased colonization with exogenously added *C. albicans* during DSS colitis in mice. However, whether colitis directly affects the makeup of the commensal fungal microbiome is not known. Notably, the inventors found that during colitis in Clec7a−/− mice the proportion of opportunistic pathogenic fungi including *Candida* and *Trichosporon* increases while the non-pathogenic *Saccharomyces* is decreased (FIG. 3B). Examination of colons revealed that fungi invade inflamed tissues in DSS-treated Clec7a−/− mice but remain in the lumen of DSS-treated WT mice (FIG. 3C and FIGS. 17, 18). These data are consistent with the observation that intestinally conditioned Dectin-1-deficient dendritic cells are less capable of killing *C. tropicalis* in vitro (FIG. 3D). Together the data suggest that Dectin-1-deficiency leads to altered immunity to commensal fungi in the gut.

Figure 22:
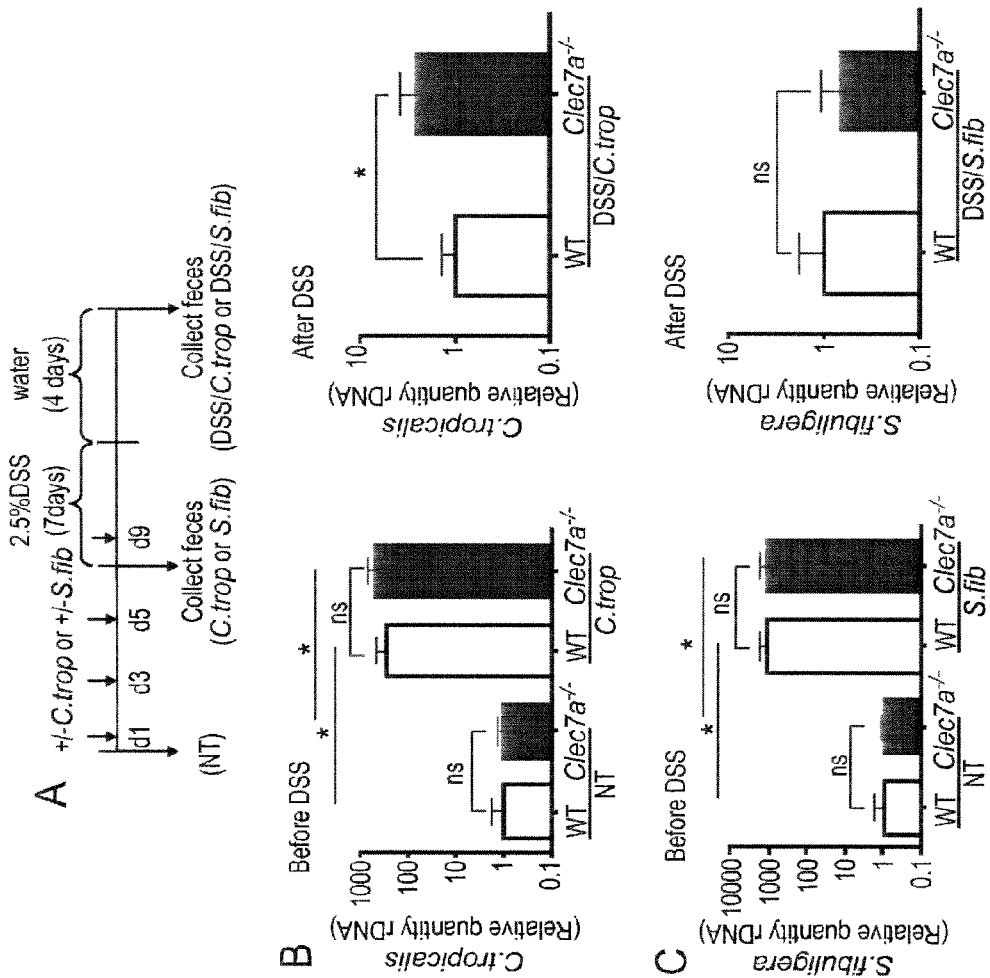
FIG. 22 depicts, in accordance with an embodiment herein, reduced clearance of supplemented *C. tropicalis* in Clec7a−/− mice during colitis (A) WT and Clec7a−/− mice were supplemented with four doses ($1×10_8$ yeast/mouse/dose) of *Candida tropicalis* (*C. trop*) or *Saccharomycopsis fibuligera* (*S. fib*) according to the schedule shown, and colitis was induced with 2.5% DSS in the drinking water for 7 days followed by 4 days of recovery. Feces were collected before supplementation with respective fungi (NT), or before (*C. trop* or *S. fib*) and after (DSS/*C. trop* or DSS/*S. fib*) DSS treatment. Feces were analyzed by qPCR for the presence of (B) *C. tropicalis* or (C) *S. fibuligera* rDNA before (B and C, left) and after (B and C, right) DSS treatment. The left panel of (B) was used in FIG. 3G and is included again here for comparison. Each symbol represents a different mouse. *P<0.05, ns (not significant). Data represent one of 2 independent experiments.
Figure 24:
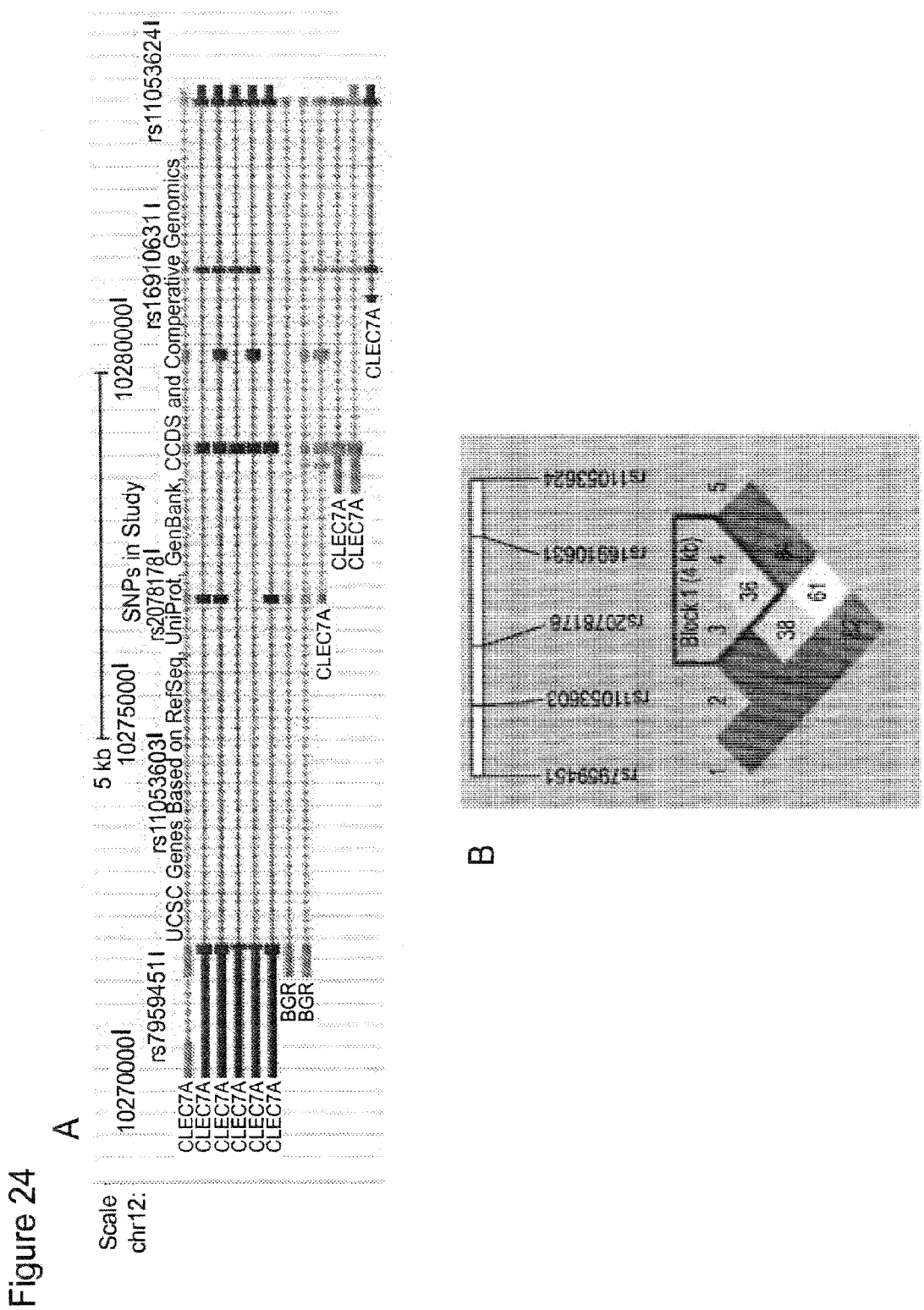
FIG. 24 depicts, in accordance with an embodiment herein, analysis of CLEC7A SNPs and haplotypes. (A) Location of CLEC7A SNPs. Cartoon of CLEC7A gene with a track showing position on Human Genome Build 37, a track showing the location of the 5 SNPs (in red) examined in this study, and a track showing exon/intron structure of transcript variants. (B) Linkage disequilibrium between CLEC7A SNPs. Using Haploview v4, linkage disequilibrium between CLEC7A SNPs was plotted; red diamonds without numbers indicate $r_2=1$. The rs2078178-rs16910631 haplotype is marked as "Block 1".

Given that *C. tropicalis* is an opportunistic pathogen, we further analyzed its role during colitis. The inventors supplemented mice with *C. tropicalis* and subjected them to DSS. For comparison, another group of mice was supplemented with *S. fibuligera*, a nonpathogenic fungus that, like *C. tropicalis*, grows in yeast and filamentous forms, and that the inventors have identified as a common commensal organism recognized by Dectin-1. They found that colitis symptoms such as weight loss, crypt loss and inflammatory cell infiltration were more severe in Clec7a−/− mice supplemented with *C. tropicalis* compared to the Clec7a−/− controls (FIG. 3E and FIG. 22B). In contrast, *C. tropicalis* supplementation did not aggravate DSS colitis in WT mice. Consistent with the pathology, they inventors detected increased IL-17 and IFN-γ production by T cells from the MLNs and colons of Clec7a−/− mice supplemented with *C. tropicalis* compared to Clec7a−/− controls (FIG. 3F and FIG. 22D). They further observed increased message for TNF-α, IL-23p19, IL-17a, Cxc12 and defensins in colons of Clec7a−/− mice supplemented with *C. tropicalis* compared to Clec7a−/− controls (FIG. 24). The observed increase in cytokine production and aggravated intestinal inflammation correlated with higher loads of *C. tropicalis* in the intestines of DSS-treated Clec7a−/− mice (FIG. 3G and FIG. 22B). In contrast, *S. fibuligera* supplementation did not contribute to colitis pathology (FIGS. 3E, F and FIGS. 19C, D and 24) and fungal loads were equivalent in the intestines of WT and Clec7a−/− mice (FIG. 25). Therefore the data suggest that an inability of Clec7a–/– mice to mount effective immune responses to specific intestinal fungi creates conditions that promote inflammation.

Figure 7:
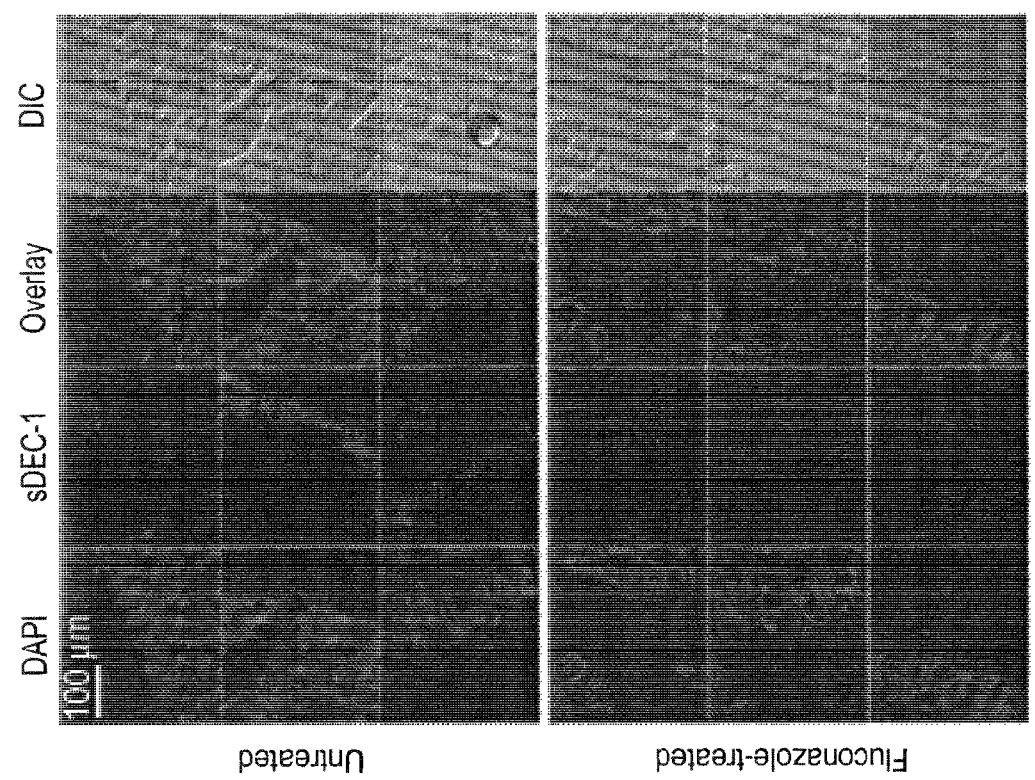
FIG. 7 depicts, in accordance with an embodiment herein, fluconazole treatment of mice depletes intestinal fungi. Mice were treated or not with fluconazole for 2 weeks, and colon sections were stained with a soluble Dectin-1 probe (sDEC-1) and counterstained with DAPI. The soluble Dectin-1 probe (red) binds to abundant luminal fungi in untreated animals, but fluconazole treatment substantially reduces the presence of fungi.
Figure 8:
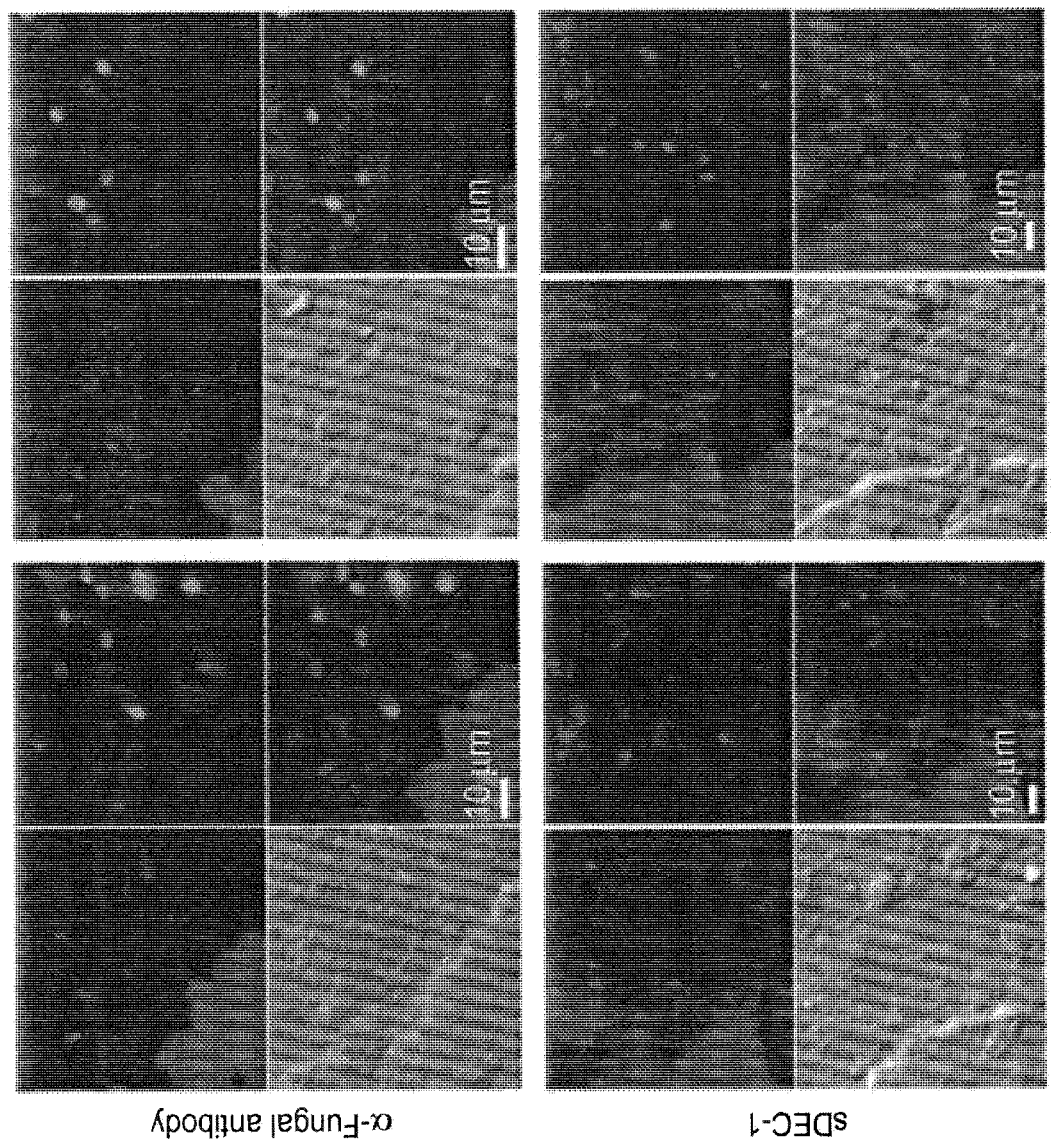
FIG. 8 depicts, in accordance with an embodiment herein, fungi and bacteria coexist in the gut. Colon sections were stained with an anti-fungal antibody (green, upper panels) or sDectin-1 (sDEC-1, red, lower panels) and counterstained with DAPI. Images were collected with long exposures to reveal DAPI binding to plentiful intestinal bacteria. Fungi are abundant and in close proximity with commensal bacteria.
Figure 9:
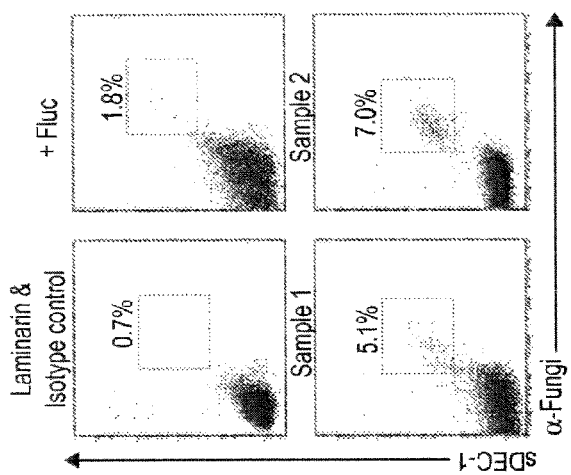
FIG. 9 depicts, in accordance with an embodiment herein, dectin-1 and an anti-fungal antibody specifically identify a substantial fungal population in feces. Fecal pellets were homogenized and labeled with soluble Dectin-1 (sDEC-1) and an anti-fungal antibody (α-fungi) and briefly stained with DAPI. The samples were analyzed by flow cytometry, gating on the DAPI-intermediate and -low fractions (lower plots, sample 1 & 2 are from two separate representative mice). To assess specificity of staining by flow cytometry, control feces were stained with sDEC-1 in the presence of soluble glucan and an isotype control antibody (upper left panel). Also feces from a mouse treated with fluconazole were stained (upper right panel). The data show that both probes identify the same population of fungi in feces.
Figure 23:
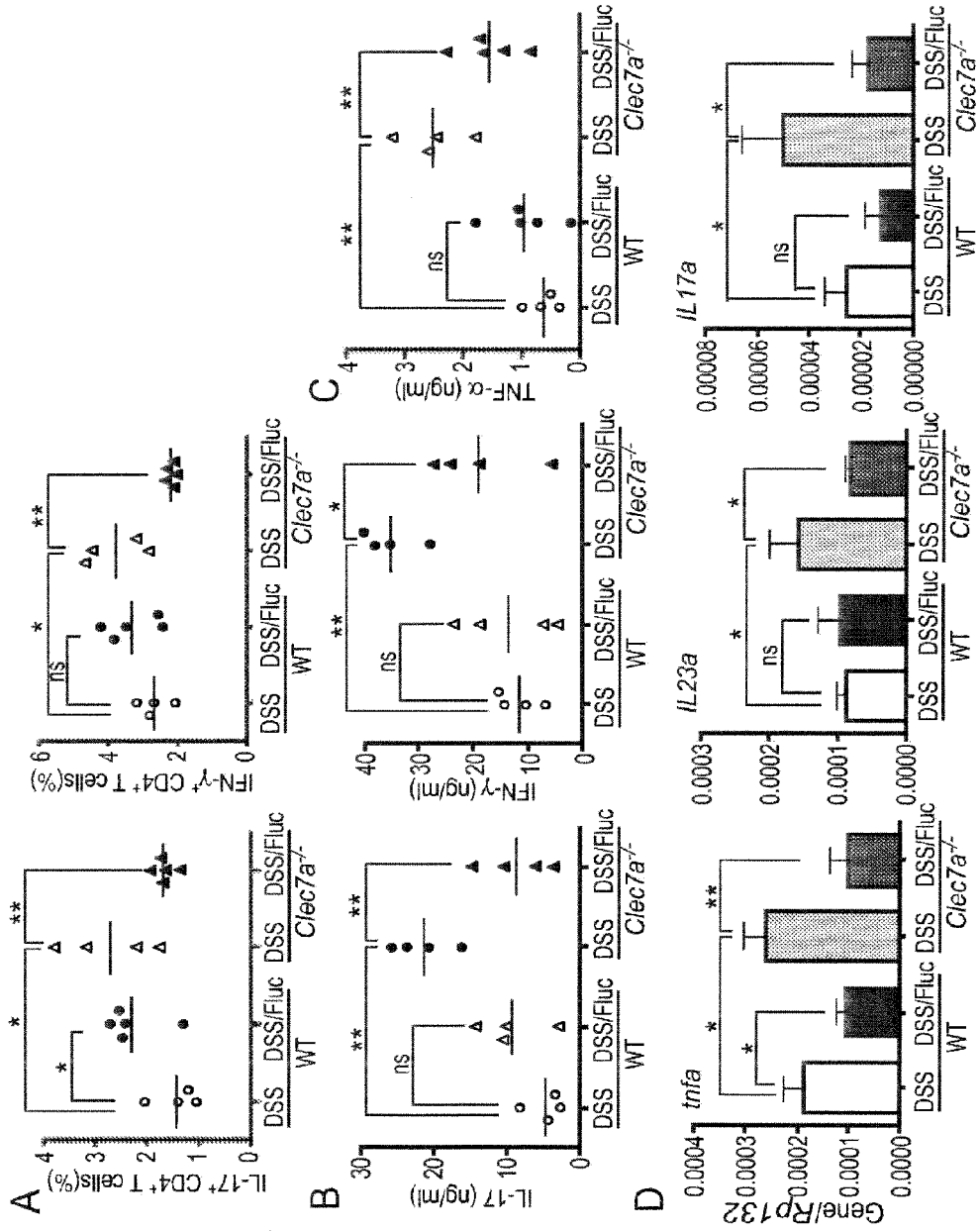
FIG. 23 depicts, in accordance with an embodiment herein, anti-fungal therapy ameliorates colitis in Clec7a−/− mice. WT and Clec7a−/− mice were given fluconazole in the drinking water for total of 14 days starting 2 days prior the induction of DSS colitis. (A) Cells were isolated and stimulated in vitro with PMA, ionomycin and Brefeldin A. Cells were permeabilized and stained with anti-CD4, anti-IL-17 and anti-IFN-γ antibodies. Samples were analyzed by flow cytometry. Graphs represent the frequency of $IL-17_+$ and $IFN-γ_+$ cells inside the $CD4_+$, T cell population. (B) IL-17 and IFN-γ produced by LI-LP, and (C) TNF-α production in the colon was determined by ELISA. (D) The expression of tnfa, 123a and III 7a in colons was measured by qPCR and normalized to Rpl32 mRNA (n=3). Data were obtained from three independent experiments with similar results. Each symbol represents a different mouse. One of three independent experiments is shown. Error bars, s.d., *P<0.05, **P<0.01.

To determine whether the altered fungal burden during colitis directly contributes to disease severity in the absence of Dectin-1, the inventors suppressed fungal growth with fluconazole, a specific anti-fungal drug (FIG. 7). The inventors found that fluconazole treatment during colitis led to reduced weight loss (FIG. 4A), and milder histological disease characteristics (FIG. 4B) specifically in Clec7a–/– mice. They similarly observed decreased Th1 and Th17 responses (FIGS. 4C, D and FIGS. 26A, B), and decreased production of inflammatory cytokines (FIGS. 23C, D). Taken together, these results further support the conclusion that an inability to control fungi in the gut leads to more severe colitis in Dectin-1 knockout mice.

Figure 4:
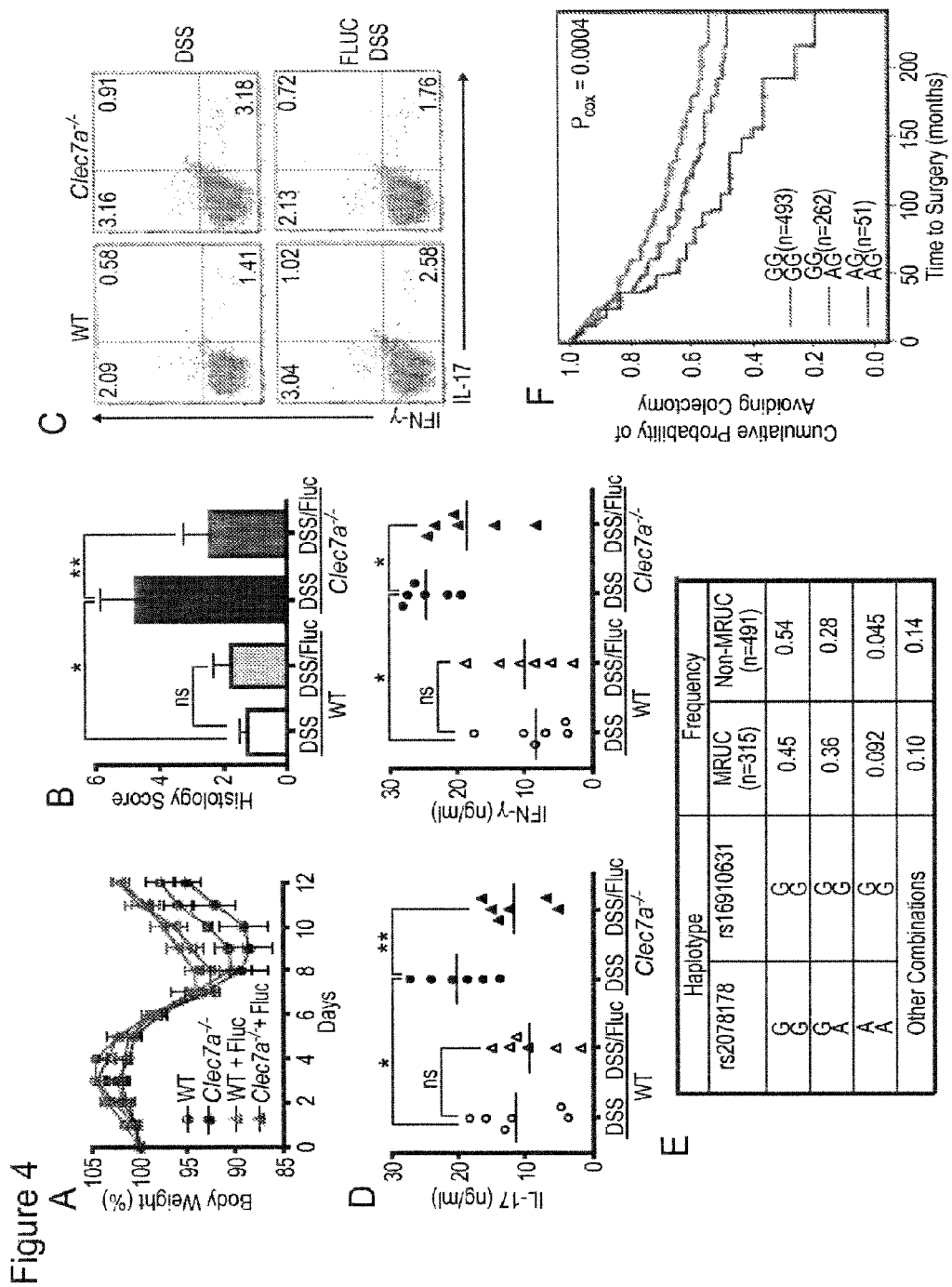
FIG. 4 depicts, in accordance with an embodiment herein, anti-fungal therapy ameliorates colitis in Clec7a-/- mice and CLEC7A associates with ulcerative colitis severity in humans. (A) WT and Clec7a-/- mice were given fluconazole in their drinking water for total of 14 days (starting 2 days prior the induction of DSS colitis), and body weight was measured. Fluconazole significantly abrogated weight loss in Clec7a-/- mice from day 9 ($p<0.05$). Histology score (B), the percentage of IL-17 and IFN-γ producing CD4+ T cells in LI-LP (C), and IL-17 and IFN-γ production in MLNs (D) were determined 4 days after the 7 days of DSS treatment. Each symbol represents a different mouse. One of three independent experiments with similar results is shown. Error bars, s.d., *$P<0.05$, **$P<0.01$. (E) Specific CLEC7A haplotypes associate with medically refractory ulcerative colitis (MRUC). Haplotypes were formed from rs2078178 and rs16910631 using PHASE v2.3. Haplotypes listed as "Other Combinations" were those that could not be reliably determined (posterior $p<0.95$). (F) The CLEC7A "AG/AG" haplotype associates with severity of disease as indicated by earlier progression to colectomy. Haplotypes were tested for association with time to surgery by fitting the MRUC/non-MRUC and time-to surgery with a Cox proportional hazards model.

Having established a role for Dectin-1 in fungal control during colitis in mice, we next explored whether there is an association between inflammatory bowel disease and genetic variation of the human Dectin-1 gene (CLEC7A). Since the mouse model suggested that Dectin-1 is involved in contributing to the severity of colonic disease, it was a logical step to focus human studies on ulcerative colitis (UC), a disease of the colon, and in particular on severe UC. Up to 30% of patients with UC require colectomy usually for severe disease that will not respond to medical therapy including systemic corticosteroids, cyclosporine and biological therapies (medically refractory UC (MRUC)). The inventors compared CLEC7A alleles in an MRUC group to a group of patients with UC who had not required colectomy (non-MRUC) (29). They identified an association of CLEC7A SNP rs2078178 in patients with MRUC (logistic regression p=0.007). Notably, a two marker haplotype, rs2078178-rs16910631, was more strongly associated with MRUC (AG haplotype; p logistic regression=0.00013/p fisher=0.0005; FIG. 4E and FIGS. 24A, B), shorter time to surgery and thus with a more severe UC (FIG. 4F). Compared to healthy controls, the haplotype is strongly associated with MRUC and not with non-MRUC, further consistent with the idea that the haplotype is associated with severe disease. CLEC7A has not been identified in any GWAS study yet as an IBD susceptibility gene. Unlike susceptibility genes which predispose to disease, severity gene variants aggravate disease that is initially established through other mechanisms. The CLEC7A risk haplotype here fits this latter situation and agrees with the observation that Clec7a–/– mice do not develop spontaneous colitis.

In summary, the gut is populated with a diverse community of fungi that has been poorly appreciated. The inventors characterize the murine gut mycobiome and show that anti-fungal host defense mediated by Dectin-1 can be an important factor in determining the severity of colitis. They observed that, similar to bacteria, some fungi are detrimental and others are not. Since they found that bacteria and fungi occupy similar niches in the gut, it will be interesting to determine to what extent the populations interact and how this may influence health and disease. They have demonstrated that Dectin-1 controls mucosal immunity to fungi in the gut and that Dectin-1-deficiency leads to exaggerated Th1 and Th17 responses and more severe disease in a mouse model of colitis. The data shows that Dectin-1 is necessary to control invasion of mucosal tissues by commensal fungi during colitis, however the receptor may also be involved in suppression of intestinal inflammation through additional mechanisms. In humans, a specific variant of the gene for Dectin-1 is strongly associated with a severe form of ulcerative colitis requiring colectomy. This can provide better therapies for IBD, and can be especially beneficial to patients with particularly severe forms of ulcerative colitis carrying the risk haplotype of the gene for Dectin-1. Overall, the idea that fungi are present in the gut and that they interact strongly with the immune system will fundamentally alter how gut microflora and inflammatory bowel diseases are viewed.

Example 3

Mice and Fungal Strains 6-10 weeks old female C57BL/6J mice were purchased from Jackson Laboratories (Bar Harbor, Me.). Clec7a–/– generated as previously described were crossed 9 generations onto the C57BL/6J background. Progeny homozygous for Clec7a–/– and wild-type littermates aged 7-12 weeks were used where indicated. All animals were housed under specific pathogen-free conditions at the Cedars-Sinai Medical Center and experiments were performed after prior approval by the Institutional Animal Care and Use Committee at Cedars-Sinai Medical Center and conformed to the policies and procedures of the Comparative Medicine Department. *Candida tropicalis* (ATCC 750) and *Saccharomyces cerevisiae* (ATCC 201388) were obtained directly from the American Type Culture Collection (Manassas, Va.). *Saccharomycopsis fibuligera* was isolated directly from murine feces and identified by rDNA sequencing. Yeasts were cultured in aerobic conditions on Sabouraud Dextrose Broth (SDB; EMD Chemicals) at 37° C.

Example 4

In Situ Staining of Intestinal Fungi

OCT-embedded intestinal specimens were sectioned, mounted on microscope slides and then incubated for 40 min in PBS containing 2% FCS. Murine soluble Dectin-1 (sDec-1) was generated and biotin-labeled as previously described. sDec-1 (10 µg/ml) was fluorescently labeled with streptavidin-Alexa 647 (2 µg/ml, Invitrogen) (sDec-1-Alexa647), and intestinal sections were stained for 1 hr. To block Dectin-1 interaction. sDec-1-Alexa647 was incubated with 1 µg/ml laminarin (soluble β-glucan from *Laminaria digitata*, Sigma) and intestinal sections were stained as previously described. Alternatively, intestinal sections were stained with FITC conjugated rabbit anti-*Candida* polyclonal antibody (Meridian Life Science, Cincinnati, Ohio). The inventors found that this "anti-*Candida* antibody" was cross-reactive with a wide variety of fungal species including *C. tropicalis, C. albicans, S. cerevisiae, S. fibuligera* and *A. fumigatus*, but did not stain bacteria (*E. coli, C. jejuni, S. aureus*). Therefore throughout this study we have referred to the antibody as an "anti-fungal antibody". Slides were rinsed with PBS and stained for 5 min with 0.1 µg/ml 4',6-diamidino-2-phenylindole (DAPI, Invitrogen) and overlaid with mounting medium (Vectashield; Vector, Burlingame, Calif.). Slides were examined using a Zeiss Axio Observer Fluorescence microscope. All compared images were collected and processed identically. Colons from Fluconazole (0.5 mg/ml for 2 weeks in the drinking water) treated mice were used in control staining.

Example 5

Staining of Fungi in the Feces

Fecal pellets were collected, homogenized in PBS containing 2% FCS and filtered through a mesh to obtain homogeneous fecal suspensions. Fecal suspensions were stained for 1 hour with sDec-1-Alexa647, anti-fungal FITC-conjugated antibody and DAPI as previously described. Control suspensions were stained with laminarin blocked sDec-1-Alexa647, FITC-labeled rabbit-IgG-isotype control antibody and DAPI. Data were analyzed by flow cytometry. To visualize intestinal fungi bound to Dectin-1, fecal samples were stained with sDec-1-Alexa647, fixed in 4% formaldehyde and sorted using a FACSAria (BD Biosciences). Sorted fungal cells were viewed using a TCS SP5 laser-scanning confocal microscope (Leica). *Detection of anti-Saccharomyces cerevisiae antibodies (ASCA)* For the induction of ASCA antibody responses to intestinal fungal antigens, mice were kept on 2.5% DSS supplemented water for 2 cycles of 7 days each. After each cycle mice were given regular water for 2 weeks. Then mice were sacrificed, blood was collected and blood serum was obtained. ELISA detection of ASCA specific IgM and IgG was carried out as previously described. Samples were read at 405 nm on a Molecular Devices E-Max microtiter plate reader (Menlo Park, Calif.).

Example 6

*Candida* Killing Assay

Intestinally conditioned dendritic cells (DCs) were prepared from WT and Clec7a−/− mice as previously described (4). *Candida tropicalis* ($1 \times 10_5$) was resuspended in RPMI 1640 supplemented with 5% fetal bovine serum (FBS) and added onto $1 \times 10_5$ DCs, and incubated at 37° C. in a 5% $CO_2$ incubator for 1 hour. Wells were washed and fresh media containing fluconazole (300 µg/ml) was added. At 6 hours and 18 hours, DCs were washed three times with PBS, lysed in water, and *C. tropicalis* CFU were calculated by plating on SDB agar.

Example 7

Induction of DSS Colitis and Histopathology

Figure 19:
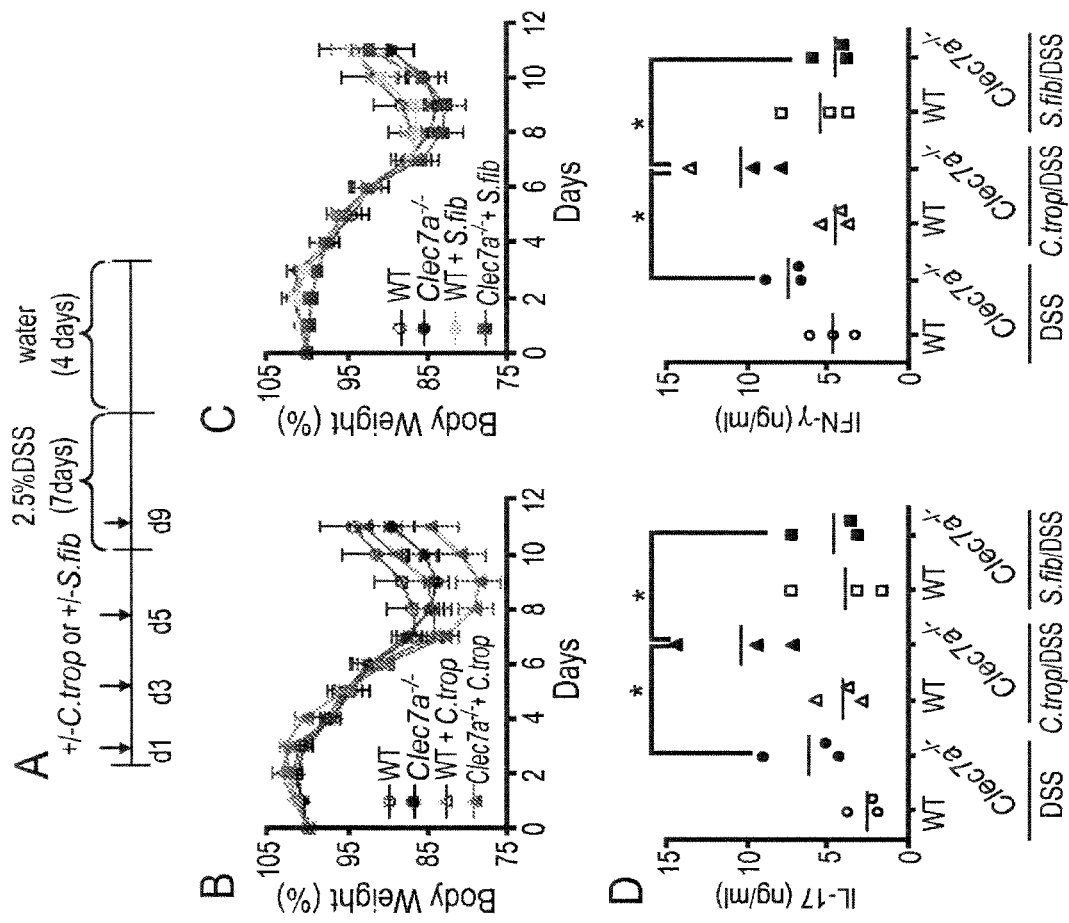
FIG. 19 depicts, in accordance with an embodiment herein, C. tropicalis but not S. fibuligera exacerbates colitis in Clec7a–/– mice. WT and Clec7a–/– mice were supplemented with four doses of C. tropicalis or S. fibuligera, treated with 2.5% DSS for 7 days and kept on water for 4 additional days (A). Graph represent body weight in WT and Clec7a–/– mice supplemented or not with C. tropicalis (B) or S. fibuligera (C) (n=–4). (D) The production of IL-17 and IFN-γ by LI-LP cells were determined by ELISA 4 days after DSS treatment (n=3). Data represent one of 2 independent experiments. Error bars, s.d., *$P<0.05$.
Figure 20:
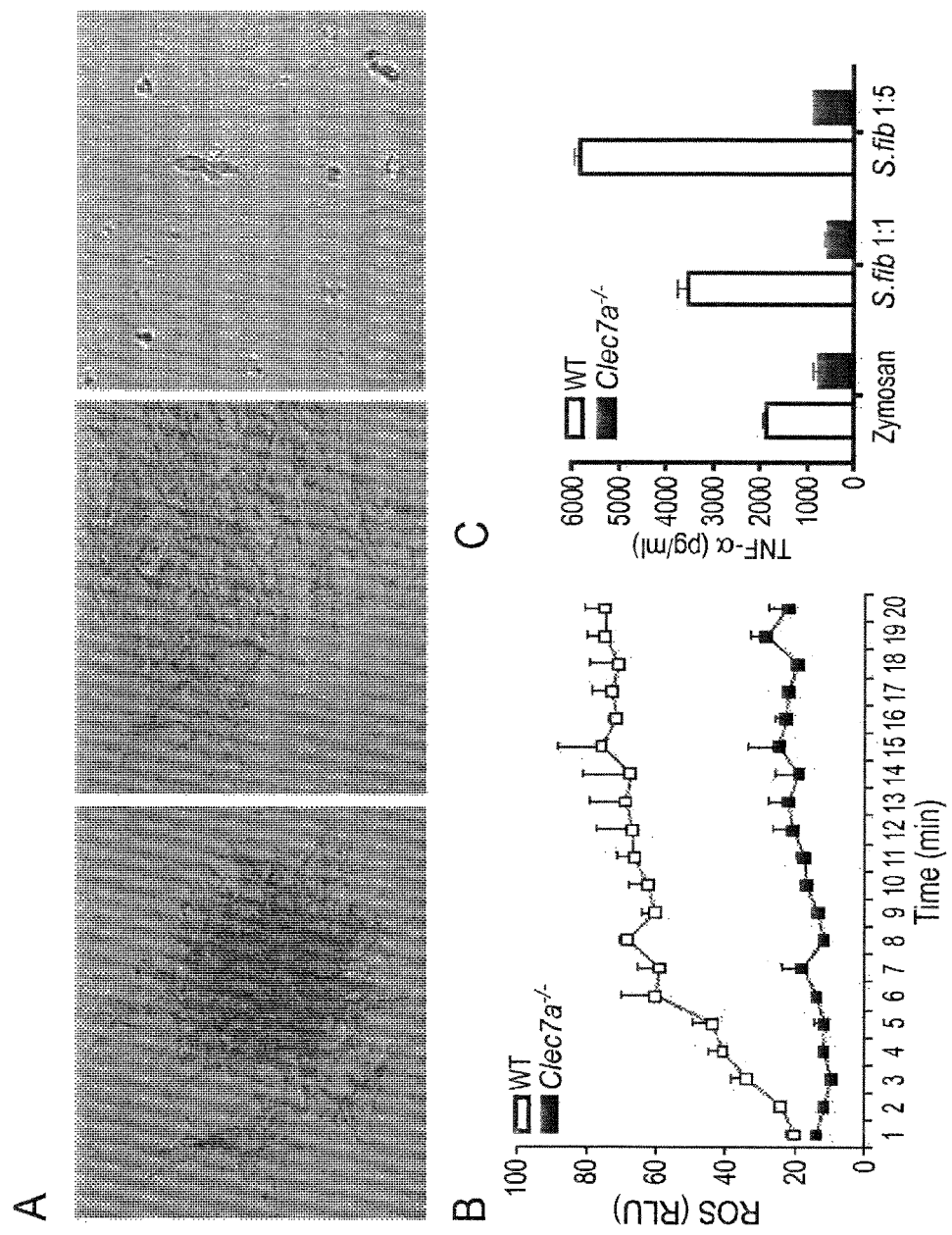
FIG. 20 depicts, in accordance with an embodiment herein, S. fibuligera is dimorphic and is recognized by Dectin-1. (A) S. fibuligera was grown on Sabouraud Dextrose Agar (SDA) to obtain filamentous form (left and middle picture) or in Sabouraud Dextrose Broth (SDB) to obtain yeast form (far right picture). (B, C) Bone marrow-derived macrophages from wild type or Clec7a–/– mice were IFN-γ-primed and stimulated with S. fibuligera (1:1). (B) Production of reactive oxygen species (ROS) was measured with luminol-enhanced chemiluminescence (ECL). (C) TNF-α production was measured by ELISA after 24 h of stimulation. Data points are means of triplicate culture. RLU, relative light units; Error bars, s.d.
Figure 21:
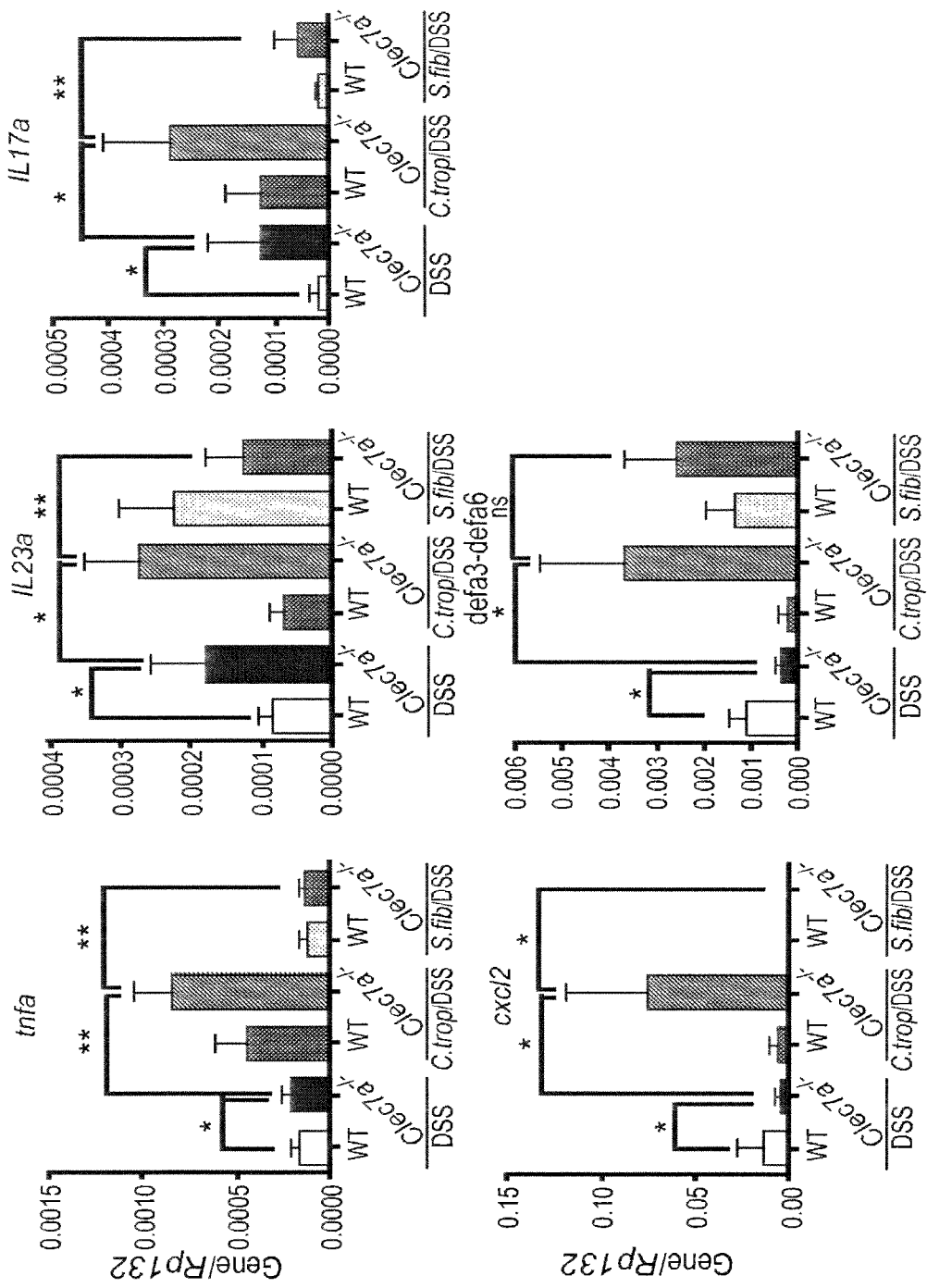
FIG. 21 depicts C. tropicalis but not S. fibuligera enhances inflammatory cytokine production in colons of DSS-treated Clec7a–/– mice. The expression of tnfa, Il23a, Il17a, cxc12 and defa3-defa6 in colons was measured by qPCR and normalized to Rpl32 mRNA (n=3) Data represent one of 2 independent experiments. Error bars, s.d., *$P<0.05$, **$P<0.01$.

WT and Clec7a−/− mice were cohoused for three weeks prior the experiments. Alternatively, WT and Clec7a−/− littermates were used where indicated. For the induction of colitis, mice were given drinking water supplemented with 2.5% (w/v) Dextran sulphate sodium (DSS, MP Biomedicals, LLC, Aurora, Ohio) for 7 days and sacrificed at day 12. For ablation of intestinal fungi, mice were given Fluconazole (0.5 mg/ml, Sigma) in the drinking water for total of 14 days starting 2 days prior the induction of DSS colitis. In some experiments, prior and upon colitis induction, mice were supplemented every other day with four doses ($1 \times 10_8$ yeast/mouse/dose) of *Candida tropicalis* or *Saccharomycopsis fibuligera* as shown in FIG. 19. Body weight, gross blood, and stool consistency were analyzed on a daily basis. Paraffin embedded colon tissues were sectioned and stained with H&E for pathology assessment. Assessment of the severity of colitis was measured by the disease activity index (DAI) as previously described.

Example 8

Antibiotic Treatment and Microbiota Reconstitution

For depletion of intestinal microbiota, mice were given an antibiotic cocktail, containing ampicillin (1 g/l; Sigma, St. Louis, Mo.), vancomycin (500 mg/l, Sigma), neomycin sulfate (1 g/l, Sigma), metronidazole (1 g/l, Sigma) and fluconazole (0.5 mg/ml, Sigma) in drinking water for 3 weeks. Fecal pellets were collected and tested for microbiota depletion by culture method (aerobic and anaerobic), sDec-1-Alexa647 staining (to evaluate depletion of fungi) and quantitative PCR. Microbiota-depleted mice were both, orally gavaged and intrarectally administrated with homogenates prepared from WT or Clec7a−/− feces, and 10 days after reconstitution DSS administration was started.

Example 9

Isolation of Intestinal Mucosa, Colonic Cells and Large Intestine Lamina Propria (LI-LP) Lymphocytes LI-LP lymphocytes were isolated as previously described with some modifications. Briefly, colons were isolated, opened longitudinally, washed of fecal contents and then cut into 1 cm pieces. Intestinal pieces were transferred into HBSS medium (Sigma), supplemented with 5% fetal bovine serum (FBS) and 2 mM EDTA, and were shaken for 15 min at 37° C. The suspensions were filtered through a mesh and the filtrate containing the mucosa and mucosa associated microflora was used further for DNA isolation. The remaining tissue was washed, cut in small pieces and subsequently incubated in digestion medium consisting of RPMI 1640, 5% FBS, 0.5 mg/ml collagenase type VIII (Sigma), 5 U/ml DNase (Roche Diagnostics), 100 IU/ml penicillin and 100 µg/ml streptomycin for 30 min at 37° C. by gentle shaking. The cell suspensions were filtered through a mesh, and then centrifuged at 1300 rpm. Cell suspensions were cultured overnight and TNF-α production by colonic cells was measured by ELISA (BioLegend, San Diego, Calif.).

The rest of the pellets were resuspended in 6 ml of 40% Percoll (GE Healthcare Bio-Sciences AB, Uppsala, Sweden), overlaid on 3 ml of 70% Percoll and centrifuged at 2000 rpm for 20 min at 25° C. The interface cells were collected and used as LI-LP lymphocytes.

Example 10

Lymphocyte Stimulation and Cytokine Analysis

Cell suspensions were prepared from MLNs and the LI-LP as described above. Cells were incubated with 50 ng/ml phorbol 12-myristate 13-acetate (PMA; Sigma-Aldrich), 500 ng/ml ionomycin (Sigma-Aldrich) and 10 µg/ml Brefeldin A (BFA; Sigma-Aldrich) in complete RPMI media at 37° C. for 6 h. After surface staining with CD4, cells were permeabilized and intracellular cytokine staining was performed using APC-labeled anti-IFN-γ mAb (XMG1.2; BD Biosciences) and PE-labeled anti-IL-17 mAb (TC11-18H10; BD Biosciences) according to the manufacturer's instructions. Flow cytometry was performed using a LSRII (BD Biosciences) and data were analyzed with FlowJo software (TreeStar Inc.).

For detection of cytokines by ELISA, MLN cells and LI-LP lymphocytes were stimulated with 10 µg/ml plate bound anti-CD3 and anti-CD28 antibodies (BioLegend, San Diego, Calif.). Supernatants were collected after 36 hrs and analyzed for IFN-γ and IL-17 production by ELISA (BioLegend, San Diego, Calif.).

Example 11

DNA Isolation, Fungal and Bacterial rDNA Gene Quantitative Analysis

Intestinal mucosa from ileum, caecum, proximal and distal colon was obtained as described above. Feces were collected from non-treated or DSS treated C57BL/6J and Clec7a−/− mice. Additionally, feces were collected from BALB/c mice, 129S2/Sv mice, Rat, Guinea Pig, Pig, Rabbit and Dog, all breed and housed in the animal facility of Cedars-Sinai medical center. Human fecal samples from 3 healthy donors were collected after obtaining informed consent and immediately frozen. Fecal or mucosal samples were resuspended in 50 mM Tris buffer (pH7.5) containing 1 mM EDTA, 0.2% β-mercaptoethanol (Sigma) and 1000 U/ml of lyticase (Sigma). The mix was incubated at 37° C. for 30 min and fungal genomic DNA was isolated by using QIAamp DNA Stool Mini Kit (Qiagen) according to the manufacturer's instructions. For evaluation of fungal rDNA in feces, 80 ng of total fecal DNA was used as a template for qPCR analysis. The following anti-fungal primers were used:

```
Target       Forward Reverse
                                   (SEQ. ID. NO.: 1)
18S rDNA 5'-ATTGGAGGGCAAGTCTGGTG-3;

(SEQ. ID. NO.: 2)
5'-CCGATCCCTAGTCGGCATAG-3'

(SEQ. ID. NO.: 3)
ITS1-2  5'-CTTGGTCATTTAGAGGAAGTAA-3;

(SEQ. ID. NO.: 4)
5'-GCTGCGTTCTTCATCGATGC-3;

(SEQ. ID. NO.: 5)
C. tropicalis 5'-TTTGGTGGCGGGAGCAATCCT-3;

(SEQ. ID. NO.: 6)
5'-CGATGCGAGAACCAAGAGATCCGT-3'

(SEQ. ID. NO.: 7)
S. fibuligera 5'-CTGCGCTTAACTGCGCGGTT-3';

(SEQ. ID. NO. 8)
5'-TGCGAGAACCAAGAGATCCGTTGC-3'
```

For detection of mucosa-associated fungi, quantitative PCR was performed on DNA isolated from intestinal mucosa using fungal-specific primers listed above. Relative quantity was calculated by the ΔCt method and normalized to the amount of β-actin (actb, for mucosal samples) or to the weight of the sample and the amount of total DNA used (for the fecal samples). The following β-actin (actb) primers were used:

```
                                   (SEQ. ID. NO.: 9)
forward primer 5'-ATGACCCAGATCATGTTTGA-3'
and (SEQ. ID. NO.: 10)
reverse primer 5'-TACGACCAGAGGCATACAG-3'.
```

Example 12

Microbiome Sequencing Analysis

Mouse fungal and bacterial microbiomes were interrogated using Roche 454 and an Illumina GAIIxe next generation sequencing platforms. DNA was isolated from feces of co-housed or littermate mice before and after DSS treatment, and from a sample of food (Mouse Diet 5015; LabDiet, St. Louis, Mo.) using the protocol described above. 454 library generation and sequencing Fungal ITS1-2 regions were amplified by PCR using primers modified to include sample barcodes and sequencing adaptors. DNA was amplified using the following PCR protocol: Initial denaturation at 94° C. for 10 min, followed by 40 cycles of denaturation at 94° C. for 30 s, annealing at 55° C. for 30 s, and elongation at 72° C. for 2 min, followed by an elongation step at 72° C. for 30 min. The PCR products containing ITS fungal regions were purified and subjected to emulsion PCR and pyrosequencing using a 454 GS FLX System (Roche Diagnostics GmbH/454 Life Sciences Corporation) at the UCLA Genotyping and Sequencing Core. Fecal DNA was amplified using the PCR protocol described above using the following primers:

```
Amplicon Forward Reverse
ITS1-2
                                   (SEQ. ID. NO.: 11)
5'-CTTGGTCATTTAGAGGAAGTAA-3';

(SEQ. ID. NO.: 12)
5'-GCTGCGTTCTTCATCGATGC-3';

16S (8F&R357)
                                   (SEQ. ID. NO.: 13)
5'-AGAGTTTGATCMTGGCTCAG-3';

(SEQ. ID. NO.: 14)
5'-CTGCTGCCTYCCGTA-3'
```

ITS1-2 and Bacterial 16S amplicons were subjected to a modified TruSeq protocol (version 2). Unique duplexed primers containing paired end adapters and indexes were ligated to the 1 μg of TS1-2 or 16S amplicons respectively. Library enrichment was performed with 10 cycles of PCR and purification was performed using Agencourt Ampure Magnetic Beads (Beckman). All libraries were subjected to quality control using qPCR, DNA 1000 Bioanalyzer (Agilent), and Qubit (Life Technologies) to validate and quantitate library construction prior to preparing a Paired End flow cell. Samples were randomly divided among flow cells to minimize sequencing bias. Clonal bridge amplification (Illumina) was performed using a cBot (Illumina). 100×150 bp sequencing-by-synthesis was performed. At 150 bps, 89% of bps were above Q30, exceeding Illumina's standard sequence quality metric.

Example 13

Data Analysis 454 data analysis: Raw sequence data were identified by their unique barcodes for each dataset and tabulated using QIIME; Unlike bacteria, the range of sequence divergence both between and within species of fungi may differ <3% in ITS-2 sequence, approaching the error rate of the 454 and making the delineation of sequence reads into OTUs less precise. To avoid spurious OTU clustering using 454 data, the inventors used an alternate approach to defining OTUs in which each unique sequence read was aligned to a previously described fungal ITS reference database using BLAST. A custom perl script was then used to parse the alignment results to identify alignments with ≥98% identity over the entire sequence read. Reads failing to align at this stringent level were discarded. The alignment results were then tabulated across all reads, using the accession identifier of the ITS reference sequences as surrogate OTUs. Over 85% of the sequences aligned with at least 98% identity to a reference sequence, which corresponds well to both the 98% mapping cut-off previously used in the analysis of the fungal mycobiome and to the inventors' own analysis of the complete dataset. Finally, the OTUs were manually curated to establish species names.

For Illumina bacterial and fungal analysis, because of the abundance of Illumina reads and higher overall sequence quality of the reads, the inventors used the QIIME package with minimal customization. Bcl files were de-multiplexed using cassava (v1.8). qSeq files were converted to FASTA files for QIIME using SAMTOOLS (12). QIIME was installed on a 400 node dual processor high performance cluster each with 4 GB of RAM. Each 150 bp fungal sequence was then BLASTed against the reference database using blastn and a cut off for a 99% nt identity match (>148/150 bps). Each result was summed across unique genbank accession numbers. For bacterial biome analysis, 150 bp single end reads from each sample were collapsed into OTUs using UCLUST and annotated.

Example 14

Rarefaction Curves

Using QIIME the inventors performed rarefaction analysis. The original OTU table was randomly subsampled (rarefied) to create a series of subsampled OTU tables. Alpha diversity was calculated on each sample using the OTU table and a variety of metrics (PD whole tree, observed species, etc). The results of the alpha diversity were collated into a single file and the number of species identified for each sample versus the depth of subsampling was plotted.

Example 15

Phylogenic Analysis

Multiple alignments were created for OTU sequences that were found in murine feces or in the mouse food. Sequences were obtained using the accession numbers in the dendrograms. Multiple alignments were performed on these sequences using Clustal W2 with a GAP open penalty of 5 and gap extension penalty of 1. Distances from the multiple alignments were then analyzed using Unweighted Pair Group Method with Arithmetic Mean (UPGMA) clustering creating dendrograms which were populated at each node with the distance between each pair wise relationship.

Example 16

Real Time PCR

Tissue samples from the proximal and distal colon were isolated and homogenized. RNA was isolated by using RNeasy Mini Kit (Qiagen) and reverse transcribed. Real-time RT-PCR analyses were done on the Applied Biosystems 7500 Fast Real-Time PCR System with the SYBR Green PCR kit as instructed by the manufacturer (Applied Biosystems). The amount of mRNA was normalized to the amount of rpl32 mRNA, a housekeeping control gene that does not change substantially during gut inflammation which we have previously used for this purpose. Samples were analyzed for gene expression using the following primers:

```
Gene Forward Reverse:
rpl32
                              (SEQ. ID. NO.: 15)
5'-AAGCGAAACTGGCGGAAAC-3;
                              (SEQ. ID, NO.: 16)
5'-TAACCGATGTTGGGCATCAG-3';

Il23a
                              (SEQ. ID. NO.: 17)
5'-GAACAAGATGCTGGATTGCAGAG-3;
                              (SEQ. ID. NO.: 18)
5'-TGTGCGTTCCAGGCTAGCA-3';

Il17a
                              (SEQ.1D. NO.: 19)
5'-CAGGACGCGCAAACATGA-3';
                              (SEQ. ID. NO.: 20)
5'-GCAACAGCATCAGAGACACAGAT-3';

Tnfa
                              (SEQ. ID. NO.: 21)
5'-TCCAGGCGGTGCCTATGT-3';
                              (SEQ. ID. NO.: 22)
5'-CACCCCGAAGTTCAGTAGACAGA-3';

defa3-defa6
                              (SEQ. ID. NO.: 23)
5'-TCCTCCTCTCTGCCCTYGTCCTG-3'
                              (SEQ. ID. NO.: 24)
5'-AGACACAGCCTGGTCTTGTcc-3';

cxcl2
                              (SEQ. ID. NO.: 25)
5'-AACATCCAGAGCTTGAGTGTGA-3';
                              (SEQ. ID. NO,: 26)
5'-TTCAGGGTCAAGGCAAACTT-3'.
```

Example 17

Statistics

Unpaired-Student's t-test was used to evaluate differences between experimental groups. Multiple groups (4-10 mice/group) were analyzed by one way analysis of variance (one way ANOVA) followed by a Tukey multiple comparisons test. Statistical analysis was performed using GraphPad Prism software (Graphpad Software Inc., San Diego, Calif.).

Example 18

Study of Medically Refractory Ulcerative Colitis

Ulcerative colitis subjects were recruited at the Inflammatory Bowel Disease Center at Cedars-Sinai Medical Center following informed patient consent and Cedars Sinai-Medical Center Institutional Review Board approval. Details of UC diagnosis was based on standard clinical, endoscopic, and histological findings; details have been previously described along with details of the definition of medically refractory ulcerative colitis (MRUC). In brief, MRUC subjects required colectomy for severe disease refractory to medical therapies. For the MRUC group, time from diagnosis to date of colectomy was obtained; for the non-MRUC group time from diagnosis to last follow-up visit was obtained. Demographics for these subjects have been previously published; in general the median follow-up of the non-MRUC group was twice that of time to colectomy of the MRUC group. Healthy controls were obtained from the Cardiovascular Health Study (CHS), a population-based cohort study of risk factors for cardiovascular disease and stroke in adults 65 years of age or older, recruited at four field centers 5,201 predominantly Caucasian individuals were recruited in 1989-1990 from random samples of Medicare eligibility lists, followed by an additional 687 African-Americans recruited in 1992-1993 (total n=5,888). CHS was approved by the Institutional Review Board at each recruitment site, and subjects provided informed consent for the use of their genetic information. A total of 3208 Caucasian non-IBD control subjects who underwent GWAS were included in these analyses. African-American CHS participants were excluded from analysis due to insufficient number of ethnically-matched cases. Genotyping was performed at the Medical Genetics Institute at Cedars-Sinai Medical Center using the Illumina Human CNV370 platform (Illumina, San Diego, Calif.). Five SNPs passing quality control spanned the CLEC7A gene (FIG. 24A); a total of 806 UC subjects with complete CLEC7A genotyping data, MRUC determination, and time to surgery or to last visit and were included in these analyses (MRUC n=315; non-MRUC n=491). The rs2078178 (SEQ. ID. NO.: 27)—rs16910631 (SEQ. ID. NO.: 28) haplotype was identified by loading the SNP data into Haploview v4 and testing for association (FIG. 24B). Assignment of haplotypes for final analysis employed PHASE v2.3. The number of each haplotype assigned is as follows:

Haplotype Number Assigned
1 AG 430
2 AA 45
3 GG 1314
4 GA 43

The greatest uncertainty in the assignment was when the subject was heterozygous for both markers. These were removed from the analysis. Haplotypes formed with probability>0.99 were tested for association with MRUC by logistic regression and Fisher's Exact Test, and for association with time to surgery by fitting with a Cox proportional hazards model (Survival package in R). Haplotypes listed as "Other combinations" were those that could not be reliably determined (posterior p<0.95). These were not included in the logistic regression or Cox proportional hazards analyses.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating an inflammatory bowel disease (IBD) in a subject, diagnosed with one or more risk variants at the Dectin-1 gene (CLEC7A), comprising:
   administering a therapeutically effective amount of an anti-fungal drug to the subject.

2. The method of claim 1, wherein IBD is ulcerative colitis.

3. The method of claim 1, wherein IBD is a severe form of ulcerative colitis.

4. The method of claim 1, wherein IBD is medically refractory ulcerative colitis (MRUC).

5. The method of claim 1, wherein IBD is based on the inability to control fungi in the gut of the subject.

6. The method of claim 1, wherein the one or more risk variants are rs2078178 (SEQ ID NO: 27), rs16910631 (SEQ ID NO: 28) or a combination thereof.

7. The method of claim 1, wherein the anti-fungal drug is fluconazole.

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Homo sapiens

<400> SEQUENCE: 1
attggagggc aagtctggtg                                              20

<210> SEQ ID NO 2
<211> LENGTH: 20
<212> TYPE: DNA
<213> ORGANISM: Homo sapiens

<400> SEQUENCE: 2
ccgatcccta gtcggcatag                                              20

<210> SEQ ID NO 3
<211> LENGTH: 22
<212> TYPE: DNA
<213> ORGANISM: Homo sapiens

<400> SEQUENCE: 3
cttggtcatt tagaggaagt aa                                           22

<210> SEQ ID NO 4
<211> LENGTH: 20
<212> TYPE: DNA
<213> ORGANISM: Homo sapiens

<400> SEQUENCE: 4
gctgcgttct tcatcgatgc                                              20

<210> SEQ ID NO 5
<211> LENGTH: 21
<212> TYPE: DNA
<213> ORGANISM: Homo sapiens

<400> SEQUENCE: 5
tttggtggcg ggagcaatcc t                                            21

<210> SEQ ID NO 6
<211> LENGTH: 24
<212> TYPE: DNA
<213> ORGANISM: Homo sapiens
```

```
<400> SEQUENCE: 6
cgatgcgaga accaagagat ccgt                                              24

<210> SEQ ID NO 7
<211> LENGTH: 20
<212> TYPE: DNA
<213> ORGANISM: Homo sapiens

<400> SEQUENCE: 7
ctgcgcttaa ctgcgcggtt                                                   20

<210> SEQ ID NO 8
<211> LENGTH: 24
<212> TYPE: DNA
<213> ORGANISM: Homo sapiens

<400> SEQUENCE: 8
tgcgagaacc aagagatccg ttgc                                              24

<210> SEQ ID NO 9
<211> LENGTH: 20
<212> TYPE: DNA
<213> ORGANISM: Homo sapiens

<400> SEQUENCE: 9
atgacccaga tcatgtttga                                                   20

<210> SEQ ID NO 10
<211> LENGTH: 19
<212> TYPE: DNA
<213> ORGANISM: Homo sapiens

<400> SEQUENCE: 10
tacgaccaga ggcatacag                                                    19

<210> SEQ ID NO 11
<211> LENGTH: 22
<212> TYPE: DNA
<213> ORGANISM: Homo sapiens

<400> SEQUENCE: 11
cttggtcatt tagaggaagt aa                                                22

<210> SEQ ID NO 12
<211> LENGTH: 20
<212> TYPE: DNA
<213> ORGANISM: Homo sapiens

<400> SEQUENCE: 12
gctgcgttct tcatcgatgc                                                   20

<210> SEQ ID NO 13
<211> LENGTH: 20
<212> TYPE: DNA
<213> ORGANISM: Homo sapiens

<400> SEQUENCE: 13
agagtttgat cmtggctcag                                                   20

<210> SEQ ID NO 14
<211> LENGTH: 15
<212> TYPE: DNA
```

<213> ORGANISM: Homo sapiens

<400> SEQUENCE: 14
ctgctgccty ccgta                                                    15

<210> SEQ ID NO 15
<211> LENGTH: 19
<212> TYPE: DNA
<213> ORGANISM: Homo sapiens

<400> SEQUENCE: 15
aagcgaaact ggcggaaac                                                19

<210> SEQ ID NO 16
<211> LENGTH: 20
<212> TYPE: DNA
<213> ORGANISM: Homo sapiens

<400> SEQUENCE: 16
taaccgatgt tgggcatcag                                               20

<210> SEQ ID NO 17
<211> LENGTH: 23
<212> TYPE: DNA
<213> ORGANISM: Homo sapiens

<400> SEQUENCE: 17
gaacaagatg ctggattgca gag                                           23

<210> SEQ ID NO 18
<211> LENGTH: 19
<212> TYPE: DNA
<213> ORGANISM: Homo sapiens

<400> SEQUENCE: 18
tgtgcgttcc aggctagca                                                19

<210> SEQ ID NO 19
<211> LENGTH: 18
<212> TYPE: DNA
<213> ORGANISM: Homo sapiens

<400> SEQUENCE: 19
caggacgcgc aaacatga                                                 18

<210> SEQ ID NO 20
<211> LENGTH: 23
<212> TYPE: DNA
<213> ORGANISM: Homo sapiens

<400> SEQUENCE: 20
gcaacagcat cagagacaca gat                                           23

<210> SEQ ID NO 21
<211> LENGTH: 18
<212> TYPE: DNA
<213> ORGANISM: Homo sapiens

<400> SEQUENCE: 21
tccaggcggt gcctatgt                                                 18

<210> SEQ ID NO 22
<211> LENGTH: 23

```
<212> TYPE: DNA
<213> ORGANISM: Homo sapiens

<400> SEQUENCE: 22
caccccgaag ttcagtagac aga                                              23

<210> SEQ ID NO 23
<211> LENGTH: 23
<212> TYPE: DNA
<213> ORGANISM: Homo sapiens

<400> SEQUENCE: 23
tcctcctctc tgccctygtc ctg                                              23

<210> SEQ ID NO 24
<211> LENGTH: 22
<212> TYPE: DNA
<213> ORGANISM: Homo sapiens

<400> SEQUENCE: 24
agacacagcc tggtcstctt cc                                               22

<210> SEQ ID NO 25
<211> LENGTH: 22
<212> TYPE: DNA
<213> ORGANISM: Homo sapiens

<400> SEQUENCE: 25
aacatccaga gcttgagtgt ga                                               22

<210> SEQ ID NO 26
<211> LENGTH: 20
<212> TYPE: DNA
<213> ORGANISM: Homo sapiens

<400> SEQUENCE: 26
ttcagggtca aggcaaactt                                                  20

<210> SEQ ID NO 27
<211> LENGTH: 1001
<212> TYPE: DNA
<213> ORGANISM: Homo sapiens

<400> SEQUENCE: 27
ccccgtgttc ctaagaagtt ttcagaaaaa gtggcactta taacacatca tgaatgaagg      60
gtagagcttc aatgaggtaa gataaggggt taataggaaa aattctatgt tataaatcta     120
aaccagtcta taacttctac acctactttc actattctta ttttgttttt gtttctgtaa     180
tgtcttaccc agtagtaata atttatatta aagttaatgg aactagatat atggcaaaga     240
aagagtactg gattacaagt ctatctgact tttaggccag cctataattg aaaataaatt     300
gttatagatt tgtaaacaat tcagatatct tcactgaacc tcagattaca tattcataaa     360
atatacagtt ggactaaatt attttttaagt tgttacctaa ctctgagaag tacttcttaa     420
cgaaagtagc gtcaatttat ttcttcaatt ggaggagaag acaatggcta atcatccatg     480
aaaactgcct aggggggactg ycatctggga ttttgtcaga taggttgaat ggaggcagta     540
cagtcctcac attacaaatc tattctttttg gaaaattaaa tgataattac tttaaataaa     600
taagataggc ttttgagac attcaatgac attcaaaaat tggcacttct ctctaggttg       660
atgtcaggtt aggcatgcat tcttttttttt tttttttgaga cggagtctcg ctctgtcgcc     720
```

```
caggccggac tgcggactgc agtggcgcaa tctcggctca ctgcaagctc cgcttcccgg       780
gttcatgcca ttctcctgcc tcagcctccc gagtagctgg gaccacaggc gcccgccacc       840
gcgcccggct aattttttgt attttttagta gagacgggggt ttcaccttgt tagccaggat     900
ggtctcgatc tcctgacctc atgatctacc cgcctcggcc tcccaaagtg ctgggattac       960
aggcgtgagc caccgcgccc ggccttgcat tctttaccaa a                          1001

<210> SEQ ID NO 28
<211> LENGTH: 121
<212> TYPE: DNA
<213> ORGANISM: Homo sapiens

<400> SEQUENCE: 28
tttattcctc tttgtgaaac tggggtaata atatctcaaa ggattattgc gggaattaaa        60
ygagctaaca catataaaag caccttgttt agagactgct agcacatgat aggtgtgttg       120
t                                                                      121
```